US008926980B2

(12) United States Patent
Mitteness et al.

(10) Patent No.: US 8,926,980 B2
(45) Date of Patent: Jan. 6, 2015

(54) # COMPOSITIONS AGAINST BACTERIAL TOXINS

(75) Inventors: Bradley M Mitteness, Ghent, MN (US); Connie Phillips, St. Peter, MN (US)

(73) Assignee: Camas Incorporated, Le Center, MN (US)

( * ) Notice: Subject to any disclaimer, the term of this patent is extended or adjusted under 35 U.S.C. 154(b) by 0 days.

(21) Appl. No.: 13/574,326

(22) PCT Filed: Jul. 11, 2012

(86) PCT No.: PCT/US2012/046215

§ 371 (c)(1), (2), (4) Date: Jul. 20, 2012

(87) PCT Pub. No.: WO2013/009843

PCT Pub. Date: Jan. 17, 2013

(65) Prior Publication Data

US 2014/0017258 A1 Jan. 16, 2014

Related U.S. Application Data

(60) Provisional application No. 61/506,379, filed on Jul. 11, 2011.

(51) Int. Cl.
*A61K 39/40* (2006.01)

(52) U.S. Cl.
USPC .................. 424/169.1; 424/164.1; 424/165.1; 530/389.5

(58) Field of Classification Search
CPC ........................... A61K 39/258; A61K 39/283
USPC ...................... 424/139.1, 169.1, 167.1, 150.1
See application file for complete search history.

(56) References Cited

U.S. PATENT DOCUMENTS 4,550,019 A * 10/1985 Polson ....................... 424/157.1
5,340,923 A 8/1994 Carroll
5,420,253 A * 5/1995 Emery et al. .................. 530/423

(Continued)

FOREIGN PATENT DOCUMENTS

RU 2127121 3/1999
WO 94/13264 6/1994
WO 2010/027473 * 3/2010 ........... A61K 39/108
WO 2010/1255565 * 11/2010 ............. C07K 16/04

OTHER PUBLICATIONS

Hirai, Kazuyuki et al, Acta Med. Okayama, 2010, vol. 64(3), pp. 163-170, Passive oral immunization by egg yolk immunoglobulin (IgY) to Vibrio cholera effectively prevents cholera.*

(Continued)

*Primary Examiner* — Gary Nickol
*Assistant Examiner* — Ginny Portner
(74) *Attorney, Agent, or Firm* — Westman, Champlin & Koehler, P.A.; Z. Peter Sawicki; Visala Goswitz

(57) ABSTRACT

Anti-toxin compositions are described that include avian antibodies against bacterial toxins. Administration of the anti-toxin compositions binds and neutralizes the bacterial toxin in the animals. Methods of making the anti-toxin compositions against the bacterial toxins are also described. The anti-toxin compositions can be effective against pathogenic bacteria and also to decrease the amount of bacterial toxins in the individual, especially in the GI tract. The anti-toxin compositions can also act as anti-inflammatory agents.

30 Claims, 8 Drawing Sheets

(56) References Cited

U.S. PATENT DOCUMENTS

| | | | | |
|---|---|---|---|---|
| 5,538,733 | A * | 7/1996 | Emery et al. | 424/422 |
| 5,585,098 | A * | 12/1996 | Coleman | 424/157.1 |
| 5,593,679 | A * | 1/1997 | van den Bosch | 424/242.1 |
| 5,599,539 | A | 2/1997 | Carroll et al. | |
| 5,601,823 | A | 2/1997 | Williams et al. | |
| 5,719,267 | A | 2/1998 | Carroll et al. | |
| 5,750,115 | A * | 5/1998 | Van Den Bosch | 424/241.1 |
| 5,762,934 | A | 6/1998 | Carroll | |
| 5,904,922 | A | 5/1999 | Carroll | |
| 5,919,665 | A | 7/1999 | Williams | |
| 6,080,400 | A * | 6/2000 | Williams et al. | 424/93.2 |
| 6,162,441 | A * | 12/2000 | Chae et al. | 424/241.1 |
| 6,214,343 | B1 | 4/2001 | Kink et al. | |
| 6,383,485 | B1 | 5/2002 | Cook | |
| 6,419,926 | B2 * | 7/2002 | Kodama et al. | 424/157.1 |
| 6,613,326 | B1 | 9/2003 | Carroll | |
| 6,706,267 | B1 * | 3/2004 | Adalsteinsson et al. | 424/157.1 |
| 6,749,831 | B1 * | 6/2004 | Bennett-Guerrero et al. | 424/1.21 |
| 6,793,921 | B2 * | 9/2004 | Kodama et al. | 424/157.1 |
| 6,797,268 | B2 * | 9/2004 | Kodama et al. | 424/157.1 |
| 6,951,742 | B1 * | 10/2005 | Duan | 435/69.3 |
| 7,256,270 | B2 * | 8/2007 | Nash et al. | 530/387.1 |
| 7,445,782 | B2 * | 11/2008 | Fairbrother et al. | 424/164.1 |
| 7,579,002 | B2 | 8/2009 | Cook et al. | |
| 8,119,147 | B2 * | 2/2012 | Emery et al. | 424/258.1 |
| 2004/0033228 | A1 | 2/2004 | Krause | |
| 2004/0086513 | A1 * | 5/2004 | Fairbrother et al. | 424/169.1 |
| 2004/0258664 | A1 * | 12/2004 | Pitcovski et al. | 424/93.2 |
| 2005/0014932 | A1 * | 1/2005 | Imboden et al. | 530/350 |
| 2005/0053604 | A1 | 3/2005 | Kink | |
| 2007/0231320 | A1 | 10/2007 | Cook et al. | |
| 2007/0264264 | A1 * | 11/2007 | Evans et al. | 424/157.1 |
| 2007/0280949 | A1 * | 12/2007 | Alfa | 424/157.1 |
| 2008/0102067 | A1 | 5/2008 | Cook et al. | |
| 2009/0092621 | A1 * | 4/2009 | Fairbrother et al. | 424/157.1 |
| 2009/0136623 | A1 * | 5/2009 | Song | 426/61 |
| 2009/0155275 | A1 * | 6/2009 | Wu et al. | 424/136.1 |
| 2011/0200610 | A1 * | 8/2011 | Ilan et al. | 424/158.1 |
| 2011/0300185 | A1 * | 12/2011 | Saeed | 424/400 |
| 2012/0135007 | A1 * | 5/2012 | Ilan et al. | 424/172.1 |

OTHER PUBLICATIONS

Arimitsu, H. et al, Protein expression and Purificaton, vol. 67, 2009, pp. 96-103.*

Cani, Patrice D. et al., "Changes in Gut Microbiota Control Metabolic Endotozemia-Induced Inflammation in High-Fat Diet-induced Obesity and Diabetes in Mice", Diabetes, vol. 57, Jun. 2008, p. 1470-1481.

Feingold, Kenneth R. et al., "Endotoxin rapidy induces changes in lipid metabolism that produce hypertriglyceridemia: low doses stimulate hepatic triglyceride production while high doses inhibit clearance", Journal of Lipid Research, vol. 33, 1992, p. 1765-1776.

Al-Attas, Omar S. et al., "Changes in ecdotoxin level in T2DM subjects on anti-diabetic therapies", Cardiovascular Diabetology, Apr. 15, 2009.

Peyrin-Biroulet, Laurent et al., "Mesenteric fat in Crohn's disease: a pathogenetic hallmark or an innocent bystander?", group.bmj.com, Sep. 6, 2006.

Erridge, Clett et al., "A high-fat meal includes low-grade endotoxemia: evidence of a novel mechanism of postprandial inflammation", American Journal of Clinical Nutrition, vol. 86, 2007, p. 1286-1296.

Harte, Alison L. et al., "Elevated endotoxin levels in non-alcoholic fatty liver disease", Harte et al. Journal of Information, vol. 7:15, 2010.

Li, Hong et al., "Intestinal, adipose, and liver inflammation in diet-induced obese mice", Metabolism Clinical and Experimental, vol. 57, 2008, p. 1704-1710.

PCT Search Report and Written Opinion; PCT/US2012/046215; Nov. 1, 2012.

* cited by examiner

COMPOSITIONS AGAINST BACTERIAL TOXINS

CROSS-REFERENCE TO RELATED APPLICATION

This Application is a Section 371 National Stage Application of International Application No. PCT/US2012/046215, filed Jul. 11, 2012, in English, which is based on and claims the benefit of U.S. provisional patent application Ser. No. 61/506,379, filed Jul. 11, 2011, the contents of which are hereby incorporated by reference in their entirety.

FIELD

The present invention relates to compositions that bind bacterial toxins. More specifically, this invention relates to avian derived antibodies that bind to bacterial toxins in mammals.

BACKGROUND

Pathogen-associated molecular patterns (PAMPs), are molecules associated with groups of pathogens that are recognized by cells of the innate immune system. These molecules can be referred to as small molecular motifs conserved within a class of microbes. They are recognized by "Toll-like receptor" (TLRs) and other "Pattern recognition receptor" (PRRs) in both plants and animals. They activate innate immune responses, protecting the host from infection, by identifying some conserved non-self molecules. Bacterial Lipopolysaccharide (LPS) found on the bacterial cell membrane of a bacterium, is considered to be the prototypical PAMP. LPS is specifically recognized by a recognition receptor of the innate immune system. Other PAMPs include bacterial Flagellin, Lipoteichoic acid from gram-positive bacteria, peptidoglycans (PGs), and nucleic acid variants normally associated with viruses, such as double-stranded RNA recognized by TLR 3 or unmethylated CpG motifs, recognized by TLR 9. Although the term "PAMP" is relatively new, the concept that molecules derived from microbes must be detected by receptors from multicellular organisms has been held for many decades.

Lipopolysaccharides are part of the outer membrane of the cell wall of gram-negative bacteria. Lipopolysaccharides are invariably associated with gram-negative bacteria whether the organisms are pathogenic or not. Endotoxin generally refers to the lipopolysaccharide complex associated with the outer membrane of gram-negative pathogens such as *Escherichia coli, Salmonella, Shigella, Pseudomonas, Neisseria, Haemophilus influenzae, Bordetella pertussis* and *Vibrio cholerae*. The term "endotoxin" is occasionally used to refer to any cell-associated bacterial toxin. While endotoxin refers to cell associated lipopolysaccharides, exotoxin refers to toxins secreted by bacteria and are predominantly polypeptides in nature.

The biological activity of endotoxin is associated with the lipopolysaccharide (LPS). Toxicity is associated with the lipid component (Lipid A) and immunogenicity is associated with the polysaccharide components. The cell wall antigens (O antigens) of gram-negative bacteria are the polysaccharide components of LPS. In addition, LPS can elicit a variety of inflammatory responses in an animal.

Gram-negative bacteria, within animals, probably release minute amounts of endotoxin while growing. This may be important in the stimulation of natural immunity. It is known that small amounts of endotoxin may be released in a soluble form by young cultures grown in the laboratory. But for the most part, endotoxins remain associated with the cell wall until disintegration of the organisms. Disintegration of the bacterial organisms can result from autolysis, external lysis mediated by complement and lysozyme, and phagocytic digestion of bacterial cells. Bacterial endotoxin is abundant in the human gut. Elevated concentrations of endotoxins are associated with a number of conditions including metabolic syndrome. Metabolic syndrome diseases include, for example, artherosclorosis, insulin resistance, diabetes mellitus, and obesity. Increased endotoxin levels have also been associated with fatty liver disease and Crohn's disease. Endotoxin may also leak out of the GI tract when present at elevated levels. Endotoxin is a potent inflammatory antigen and leaking of the endotoxin can result in systemic inflammatory response.

Compared to the classic exotoxins of bacteria, endotoxins are less potent and less specific in their action, since they do not act enzymatically. Endotoxins are heat stable (boiling for 30 minutes does not destabilize endotoxin), but certain powerful oxidizing agents such as superoxide, peroxide and hypochlorite, have been reported to neutralize them. Since these are powerful oxidizing agents they are not particularly amenable to a therapeutic composition for neutralizing endotoxins.

There are a number of other molecules that can also act as bacterial toxins. Gram-negative bacteria can also produce a number of other toxins such as Shiga toxin and leukotoxin. These may be associated with the cells or they may also be secreted by the cells into the extracellular space. Peptidoglycans are also associated with bacteria, especially gram-positive bacteria. The peptidoglycan layer in gram-positive bacteria is substantially thicker than in gram-negative bacteria. The peptidoglycan layer is about nine times thicker in gram-positive bacteria than in gram-negative bacteria. Peptidoglycans are associated with cell walls. Capsular polysaccharides are another bacterial component associated with the cells in both gram-positive and gram-negative bacteria.

SUMMARY

Figure 1A:
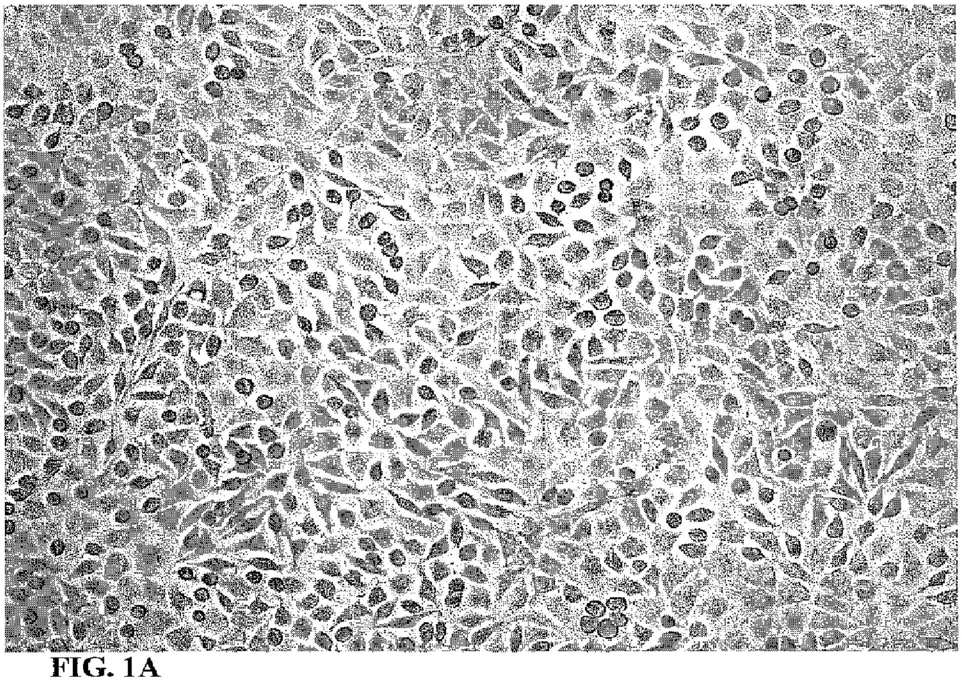
FIG. 1A is a micrograph that shows L929 cells without toxin or antibody.

In a first aspect, the present invention includes an anti-toxin composition. The anti-toxin composition includes avian antibodies derived from an egg or eggs of a bird inoculated with an inoculum comprising bacterial toxin, the antibodies capable of binding a bacterial toxin.

In a further aspect, the present invention includes a method of making an anti-toxin composition. The method includes administering an inoculum comprising a bacterial toxin to a bird and harvesting the antibodies from the egg contents derived from the bird, wherein the harvested antibodies bind to the bacterial toxin.

In another aspect, the present invention includes a method of reducing bacterial toxins in an animal. The method includes administering an anti-toxin composition comprising avian antibodies derived from the egg contents of a bird immunized with an inoculum comprising a bacterial toxin, wherein the antibodies bind the bacterial toxin.

In yet another aspect, the present invention includes a method of treating a disease. The method includes administering an anti-toxin composition comprising avian antibodies derived from the egg contents of a bird immunized with an inoculum comprising a bacterial toxin, wherein the disease is caused by increased levels of bacterial toxins.

In a yet a further aspect, the present invention includes an anti-toxin composition comprising avian antibodies derived from an egg or eggs of a bird inoculated with one or more bacterial immunogens, wherein the antibodies are capable of binding a bacterial toxin.

In an additional aspect, the present invention includes method of making an anti-toxin composition. The method includes administering a bacterial immunogen to a bird wherein the bacterial immunogen comprises a bacterial toxin and harvesting the antibodies from the egg contents derived from the bird, wherein the harvested antibodies bind to the bacterial toxin.

DETAILED DESCRIPTION

The present invention relates to compositions that bind bacterial toxins. The compositions generally include antibodies derived from an avian that are capable of binding and/or neutralizing the bacterial toxins. The bacterial toxins may be within the cells, attached to cell walls or secreted from the bacterial cells. The antibodies can be harvested from the eggs of birds immunized with an inoculum that includes one or more bacterial toxins. The bacterial toxins can be from gram-positive bacteria or gram-negative bacteria. The bacterial toxin in the inoculum may be in a purified form. Alternatively, the bacterial toxin may be attached to whole cells or to cellular fragments. Bacterial toxins can include, for example, lipopolysaccharides (LPS), Shiga toxin, peptidoglycans and the like. In particular, the present invention relates to anti-toxin compositions that include antibodies that bind and/or neutralize the bacterial toxins. Preferably, the antibodies neutralize the bacterial toxins and prevent or reduce triggering the inflammatory response of the animal.

Chronic exposure to bacterial toxins such as endotoxins can lead to a systemic inflammatory response in animals. Advantageously, administration of the anti-toxin composition can lead to a decrease in the inflammatory response in the animal. In other words, binding of the bacterial toxins by the avian antibodies can result in dampening the inflammatory response, preferably the decrease in the inflammatory response is systemic. Thus, the anti-toxin compositions of the present invention can act as anti-inflammatory agents.

The anti-toxin compositions described herein are generally specific to the pathogenic bacteria or to the specific bacterial toxins against which they were raised. Surprisingly, anti-toxins can be isolated that have sufficient specificity that only the pathogenic or "undesirable" bacteria or toxins are targeted while the "desirable" bacteria are unaffected. The GI tract, for example, is populated by vast numbers of beneficial *E. coli*. The anti-toxin composition is advantageously not deleterious toward these beneficial microbes. The anti-toxin composition can be prepared to target only the bacterial toxins that may be present in the host. Alternatively, the anti-toxin composition can be prepared to target known or new pathogenic bacterial isolates.

The present invention also relates to methods of producing the anti-toxin compositions that include the antibodies to bacterial toxins. Bacterial immunogens can be prepared by growing the bacterial cells as described herein to steer the bacteria to produce the toxins at desired levels. Bacterial immunogens can be the whole cells or cell fragments grown in this manner. Alternatively, the bacterial immunogens can be toxins produced by and isolated from bacterial cells. The bacterial toxins in the inoculum may be in a purified form or may be attached to whole cells or to cellular fragments. The method can include administering an inoculum that includes the bacterial immunogens to a bird and after the appropriate time period collecting the eggs and harvesting the egg contents. The entire egg contents may be used. Alternatively, the antibodies can be partially or completely purified from the egg contents. The method also may include suspension of the antibodies in acidified water or buffer to make the anti-toxin composition.

The present invention also relates to methods for binding and/or neutralizing the bacterial toxins in an animal. The method can include administering an anti-toxin composition that includes avian antibodies to the animals. The anti-toxin, when administered to the animal, can bind to and/or neutralize at least some of the bacterial toxin in the animal. The antibodies in the anti-toxin composition may interact with the bacterial toxins at a variety of locations in the animal such as the bloodstream, liver and the like. The anti-toxin may interact, for example, with the bacterial toxin in the GI tract. Alternatively, it can interact with the bacterial toxin after it has leaked out of the GI tract.

The present invention also relates to methods of treating a variety of diseases, especially diseases associated with metabolic syndrome. The method can include administering an anti-toxin composition to the animal in sufficient amounts to reduce the amount of bacterial toxins present in the gut and also to dampen the inflammatory response in the animal.

The anti-toxin compositions of the present invention generally include antibodies. "Anti-toxin" as used herein relates to an anti-toxin composition that includes antibodies capable of binding and/or interacting with the bacterial toxins described herein. When the antibodies bind or interact with the bacterial toxins, they can neutralize, disrupt and/or inactivate the bacterial toxin. The antibodies can bind with the bacterial toxins and engender a decrease in the activity of the bacterial toxin. In some exemplary embodiments, the antibodies can lead to agglutination of the bacterial toxins in the GI tract, thus, preventing the release of the bacterial toxins from the GI tract.

The anti-toxin compositions described herein preferably include avian antibodies. Avian antibodies can be an attractive product for producing antibodies for a number of reasons. All mammals and birds provide protection, which allow for an immediate immune response in their very young offspring until they acquire the ability to make the antibodies for themselves. More specifically called passive antibody protection, this defense mechanism is passed to the young of mammals through the placenta, the mother's milk, or through both. The young of birds, however, receive their passive antibody protection through the store of antibodies placed in the eggs in which they develop from the embryonic stage. Birds, in particular, have the ability to "load up" their eggs as they are formed, with a very large supply of antibodies concentrated over that which is present in the serum of the mother. In addition, avian antibodies are much more stable and resistant to inactivation through digestion than mammalian antibodies, especially under adverse conditions. Once immunized, the hen deposits IgY type immunoglobulins in the yolk while depositing IgM and IgA immunoglobulins in the albumin. The albumin helps add stability to the whole egg preparations and helps protect the avian antibodies. Furthermore, a large fraction of the antibodies deposited in the eggs by the hen are against the most recent antigenic challenges to the hen. This all results in the eggs of birds being a most ideal source for large quantities of economically produced highly specific and stable antibodies. While the invention is illustrated by the use of chickens to produce avian antibody, other fowl including turkeys, ducks, geese, ostrich, emu, pheasant, pigeon, quail, etc. or combination thereof, may be used.

In the present invention, the antibodies can be obtained from birds that have been inoculated with an inoculum that includes an immunogenic bacterial toxin. Eggs from these inoculated birds can be collected and the contents of the eggs harvested to obtain the antibodies. In one exemplary embodiment, birds, such as hens, are inoculated with one or more types of immunogenic bacterial toxins. After some period of time, eggs from hens inoculated with the bacterial immunogens are harvested. The contents of the eggs are separated from the shells. The egg contents generally include binding material that can bind and neutralize bacterial toxins. In preferred embodiments, the contents of the eggs include antibodies that can bind and neutralize the bacterial toxins. The contents of the eggs may be used with or without further purification. This anti-toxin composition may be a water-based product or a powder.

An "immunogen" as used herein is a specific type of antigen and is a substance that is able to provoke an adaptive immune response if injected on its own. An "antigen" is able to combine with the products of an immune response. All immunogens are antigenic, however all antigens are not necessarily immunogenic.

"Bacterial immunogens" as used herein can include whole cells, cellular fragments, purified or substantially purified bacterial toxins or combinations thereof. When whole bacterial cells are used as bacterial immunogens, the whole cells include bacterial toxins attached to the cell walls or cell surfaces. The bacterial cells may include genes or other macromolecules that increase the occurrence of the bacterial toxins associated with the cells.

Bacterial immunogens can include any of the bacterial toxins described herein. The bacterial toxin can be a purified preparation. Alternatively, the bacterial toxin may be part of whole cells or cellular fragments. Bacterial immunogens may include one kind of toxin such as endotoxin or Shiga toxin. Alternatively, bacterial toxin in an inoculum may include more than one type of toxin, for example, a combination of Shiga toxin and endotoxin. The bacterial immunogens in an inoculum may include only whole cells or it can include a combination of whole cells and one or more bacterial toxins that are not attached to cells or cell fragments. Cell surface molecules such as adhesins are not desirable as bacterial immunogens described herein.

The bacterial immunogens in an inoculum used to inoculate birds may include more than one bacterial toxin, for example, a combination of endotoxin and Shiga toxin. Bacterial immunogens used to inoculate birds may be from one bacterium. Alternatively, the bacterial immunogens used to inoculate birds may include immunogens of two or more different bacteria. These immunogens from the different bacteria can be combined prior to inoculating the birds.

In some preferred embodiments, each bird is inoculated with an inoculum that includes one kind of bacterial immunogen, i.e. a specific bacterium or a bacterial toxin. The egg contents from birds that are inoculated with whole cells and the egg contents from birds that are inoculated with a toxin may be combined to form a polyvalent anti-toxin composition. For example, after the eggs are harvested, the egg contents derived from the different birds may be combined to obtain an anti-toxin composition that has polyvalent antibodies. Alternatively, eggs can be harvested and the antibodies purified from the different birds. Purified antibodies may then be combined to form a polyvalent anti-toxin composition.

Bacterial toxins as referred to herein relate to toxins generated from bacteria and can be from gram-negative and/or gram-positive bacteria. The bacterial toxins may be associated with the cells, cell walls or cell membranes. Alternatively, the bacterial toxins can be exotoxins, i.e. toxins may be secreted out of the cell. The bacterial toxin may be a purified, unpurified, or partially purified preparation. The bacterial toxins can be the lipopolysaccharide (LPS) component of bacteria, particularly gram-negative bacteria. LPS is commonly also referred to as endotoxin. "LPS" and "endotoxin" will be used interchangeably and can be considered as equivalent. The bacterial toxins may also be the peptidoglycan (PG) component of bacteria, particularly when the toxins are from gram-positive bacteria. LPS and PG can be associated with whole cells and/or cellular fragments caused from lysis of the cells. The LPS and PG can also be free from other cellular material. Capsular polysaccharides can also function as bacterial toxins. The antibodies can bind a variety of other bacterial toxins. Bacterial toxins can include endotoxin, Shiga toxin, leukotoxin, SLT1, LST2, EAE, STb, VacA, Cag1, LPS, capsular polysaccharide, peptidoglycans, A and B toxins from, for example, *Clostridium difficile* and the like. Bacterial toxins may be naturally occurring toxins in the bacteria. The bacterial toxin may or may not be derived from expression of the toxin using recombinant DNA methods. Other bacterial toxins are also within the scope of this invention.

A variety of gram-positive and gram-negative bacteria can be sources of the bacterial toxins and the bacterial immunogens described herein. Gram-negative bacteria include, for example, *Escherichia coli, Helicobacter pylori, Klebsiella pneumoniae, Mannheimia haemolytica, Biebersteinia trehalosi, Actinobacillus suis, Haemophilus parasuis, Pasteurella multocida, Fusobacterium necrophorum* and the like. Gram-positive bacteria include, for example, *Streptococcus pyogenes, Staphylococcus hyicus, Staphylococcus aureus, Streptococcus suis, Streptococcus iniae, Streptococcus agalactiae, Clostridium difficile, Clostridium perfringens* and the like. Microorganisms can also include *Mycoplasma hyosynoviae, Mycoplasma bovis, Mycoplasma hyopneumoniae*. Bacterial toxins and bacterial immunogens derived from other gram-negative and gram-positive bacteria are also within the scope of this invention.

Examples of bacteria and bacterial toxins are listed in Table 1-4. The antibodies produced can be used with any gram-negative microorganism(s) which produce lipopolysaccharides (LPS) during their life cycle. Specifically, the examples of such Shiga Toxin *Escherichia coli* (STEC) such as those listed in TABLE 1 and LPS or other toxin producers TABLE 2.

Examples of Gram positive microorganisms that produce a potent cytotoxin, pore-forming toxin, or strong polysaccharide capsule (Table 3) are also suitable for use in the production of specific antibodies for the product mixture. Additional microorganisms suitable for use as immunogens in the avian antibody scheme are also listed in TABLE 4.

TABLE 1

| Microorganism | Gram characteristics | Designation (confirmed by PCR) | Toxin(s) [confirmed by PCR or other test method] |
|---|---|---|---|
| *Escherichia coli* | Gram − | O157:h7 | SLT1, SLT2, EAE, LPS, |
| *Escherichia coli* | Gram − | 0141:h4 | SLT2, STb, LT, LPS |
| *Escherichia coli* | Gram − | 0111:B4 | Shiga, LPS |

TABLE 2

| Microorganism | Gram Characteristics | Designation (confirmed by PCR) | Toxin(s) |
|---|---|---|---|
| *Escherichia coli* | Gram − | 0149:H19 | LT, STb, LPS |
| *Klebsiella pneumoniae* | Gram − | | LPS |
| *Helicobacter pylori* | Gram − | | VacA, Cag1 |
| *Mannheimia haemolytica* | Gram − | | Leukotoxin, LPS |
| *Bibersteinia trehalose* | Gram − | | Leukotoxin, LPS |
| *Actinobacillus suis* | Gram − | | LPS |
| *Haemophilus parasuis* | Gram − | | LPS |
| *Pasteurella multocida* | Gram − | | LPS, capsular polysaccharide, LT |
| *Fusobacterium necrophorum* | Gram − | Var necrophorum, Type A | LPS |

TABLE 3

| Microorganism | Gram characteristics | Designation (confirmation | Toxin(s) |
|---|---|---|---|
| *Streptococcus pyogenes* | Gram + | | peptidoglycan |
| *Staphylococcus hyicus* | Gram + | | EXFOLIATIVE |
| *Staphylococcus aureus* | Gram + | | peptidoglycan |
| *Streptococcus suis* | Gram + | St 2B | Capsular polysaccharide, Peptidoglycan, |
| *Streptococcus iniae* | Gram + | Aquatic | Capsular polysaccharide peptidoglycan |
| *Streptococcus agalactiae* | Gram + | Aquatic | Capsular polysaccharide peptidoglycan |
| *Clostridium difficile* | Gram + | | A and B |
| *Clostridium perfringens* | Gram + | Type A | |

TABLE 4

| Microorganism | Gram characteristics | Designation |
|---|---|---|
| *Mycoplasma hyosynoviae* | NA | |
| *Mycoplasma bovis* | NA | |
| *Mycoplasma hyopneumoniae* | NA | |

The anti-toxin compositions can include antibodies against one or more of the bacterial toxins. In some preferred embodiments, the anti-toxin compositions include antibodies against more than one bacterial toxin. Anti-toxin compositions having antibodies against only one bacterial toxin are referred to herein as a monovalent composition. Anti-toxin compositions having antibodies against more than one bacterial toxin are referred to herein as polyvalent compositions.

The antibodies in the anti-toxin composition can be derived from the egg content of a single egg or multiple eggs laid by the same bird. The anti-toxin composition may also include antibodies that are derived from a group of birds wherein all the birds in the group have been inoculated with the same bacterial immunogens. Alternatively, the anti-toxin composition may include antibodies that are derived from egg contents of birds that have been inoculated with different bacterial immunogens. Egg contents from birds inoculated with various bacterial immunogens can be pooled together and used as described herein. The anti-toxin composition may be monovalent or polyvalent.

The anti-toxin composition can include unpurified, partially purified or substantially purified antibodies obtained from avian eggs. The anti-toxin composition can include egg contents that have not been purified. Egg contents of birds inoculated with a bacterial immunogen can have a high concentration of the desired antibody and thus the egg contents may be used without any further purification of the antibody. By partially purified, it is meant that some processing or purification steps may be performed but there are still a number of other egg components still present in the composition. By substantially purified, it is meant that the antibody preparation is free from most other non-protein or non-antibody molecules but some other egg component may still be present. By substantially purified, it is meant that the antibody preparation generally includes at least about 85 percent by weight of protein/antibody, preferably at least about 95 percent by weight and most preferably, at least about 99 percent by weight of protein/antibody.

The anti-toxin composition may include other additives in addition to the antibodies and egg-derived components. These additives can include, for example, molasses or more pure sugars, soy oil, cell culture media such as DMEM, PBS buffer, Vitamin E solution and the like. Additives, for example, carriers may be added to the anti-toxin composition to enable improved administration and/or absorption by the animal.

The egg contents may be purified using one or more steps to obtain a higher concentration of antibodies in the anti-toxin composition. Purification may include, for example, centrifugation, PEG precipitation, affinity chromatography, tangential flow filtration (TFF) and the like. PEG precipitation may be performed, for example, using kits from Promega, Madison, Wis. TFF may be done according to the Pall Corp., Port Washington, N.Y. One or more of these purification procedures may be practiced on the egg contents to obtain a higher concentration of the product. Other purification procedures are also within the scope of this invention.

The amount of antibody in an anti-toxin composition can vary and is dependent on the use, the toxin that needs to be neutralized, the type of animal, the size of the animal, etc. In some exemplary embodiments, the concentration of the protein/antibody in the composition is at least about 1 mg/ml. Preferably, the concentration is at least about 3 mg/ml. The anti-toxin composition, however, may be diluted prior to use. The composition, for example, may be diluted from about 1:2 to about 1:1000. Any dilutions of the antibody solution or the anti-toxin composition are within the scope of the invention.

The antibodies can be stored in a liquid form or a dry form. If the antibody is in a dried form, it can be stored at room temperature for over 3 years without losing antibody activity. In a liquid form, the antibodies may be stored under refrigeration conditions for at least about 6 months. The dried form of the antibodies may be dissolved or resuspended in acidified water or acidified buffer prior to use. Additives may be added after resuspension in liquid.

The antibodies in a liquid composition are preferably under acidic conditions, i.e. pH less than 7. Avian antibodies generally have pKa's that are below 7 and the pH of the solution is preferably about the same as the pKa of the antibody. More preferably, the pH of the anti-toxin composition is between about between 4.5 and about 6.5. In some preferred embodiments, the antibodies are in a composition with acidified water or acidified buffer such as acidified PBS. Acidified water as used herein relates to water having a pH lower than 7. Acidified buffer as used herein relates to a buffer having a pH lower than 7.

The anti-toxin composition may be administered in a variety of methods including orally, nasally, intravenously, intraperitoneally and the like. The anti-toxin composition can be administered to any animal, for example, beef cattle and dairy herds, swine, companion animals, high value nonfood animals, zoological animals and humans. Preferably, the animal is a mammal.

The present invention also relates to methods of making the anti-toxin compositions. The method includes inoculating birds with the bacterial immunogens described above. Specifically, groups are obtained of young hen chickens, typically Rhode Island Reds, White Leghorns, sex-linked hybrid crosses or other breeds suited to large egg size, high volume egg production and ease of handling which are about to reach laying age, about 16-19 weeks for chickens, on a schedule predetermined by the amount and timing of final product desired resulting in a steady continuous production stream. After a suitable period of isolation and acclimatization of about two to four weeks, each group will enter into an inoculation program using preparations of bacterial immunogens to which an antibody is desired. Bacterial immunogens are as described above. The cultures of microorganisms may be obtained from commercial sources such as the American Type Culture Collection (ATCC) or from wild type isolates. The cultures may be used to isolate antigens. The antigens can be prepared as immunogens and may be injected subcutaneously, but preferably injected intramuscularly. In approximately four to five weeks, the average egg collected will contain copious amounts of the desired specific antibody in a readily usable and stable form. The chickens may be reinoculated with the targeted immunogen throughout the egg laying period to maintain the high antibody level.

Generally, in order to prepare bacterial immunogens for inoculation into birds, the bacterial cells are grown in a manner that provides for increased production of the desired bacterial toxin. In an exemplary embodiment, to prepare a batch of Shiga toxin containing *E. coli* O157:h7 cells (STEC) for use as bacterial immunogens, cells are confirmed to contain the Stx1 and the Stx2 genes. These genes are involved in expression of Shiga toxin. Conditions are manipulated, for example, to increase the expression of these Shiga toxin genes. Similarly, the DNA or the growing conditions of other bacteria can be manipulated to maximize the expression of the desired bacterial immunogen. In some embodiments, only naturally occurring bacterial toxin or toxin derived from a naturally occurring gene are used. Bacterial toxins obtained using recombinant DNA methods can also be within the scope of this invention Example 1 below describes exemplary protocols for growth and preparation of gram-negative and gram-positive microorganisms. The protocols in the Example are illustrative and other methods of growth and preparation of the microorganisms are also within the scope of this invention. Briefly, the microorganisms are grown in media, either in broth or agar plates suitable for whole cell growth and capsular components. Growth can be under aerobic or anaerobic conditions and at temperatures that are comparable to the normal growth site such as the nasal cavity or in the gastrointestinal tract (GI). For example, organisms found in the nasal cavity are grown at about 34° C., whereas organisms found in the GI are grown between about 36-39° C. After growth, cells are harvested into a buffer having a pH at the isoelectric point of the toxin. The solution with the cells are centrifuged and the cells are separated from the supernatant. The cells, the supernatant or both can be used for further processing based on the desired bacterial immunogens. Exemplary growth conditions for gram-positive bacteria are also described in Example 1. Whole cells of gram-positive bacteria may be used. Some purification of the cells, for example, to enhance the peptidoglycan content may also be performed.

The inoculum used for immunizing the birds generally includes immunogenic bacterial toxin. The bacterial toxin may be a purified, partially purified or unpurified preparation of bacterial toxin that is not associated with cells or cell fragments, i.e. free bacterial toxin. The inoculum can include bacterial toxin that is associated with whole cells or cellular components. The inoculum may include a combination of bacterial toxin associated with cells or cell components as well as free bacterial toxin. Any combinations of bacterial toxins may be included. The inoculum may include more than one bacterial toxin derived from the same type of bacterium or from different type of bacterium. In some preferred embodiments, the inoculum includes one bacterial toxin in only one form (either free or associated with cells). The inoculum may also include other components such as adjuvants and other carriers to enhance the immunogenicity of the inoculum.

After the birds have been immunized, eggs from the birds are collected after an appropriate time. Generally, the birds are inoculated for between about 4 to about 8 weeks. The inoculation may be also for longer or shorter duration. Egg collection, for example, may be started at about 10-14 days after the last inoculation. Eggs that have been collected before 10 days and after 14 days may also be used for collecting the egg contents.

Batches of eggs from predetermined groups of chickens are cracked; the contents are separated from the shells. Either whole egg (yolk+white) or yolk only may be used. "Egg contents" as used herein can refer to whole egg contents or yolk only. Egg contents may be further processed by the addition of acidified water or an acidified buffer such as acidified PBS. The mixture may be chilled and further processed.

Further processing can include a variety of processing steps and/or purification steps. Exemplary steps and protocols include centrifugation, PEG precipitation, affinity chromatography, tangential flow filtration (TFF) and the like. The products may also be pasteurized. Other processing and purification steps may also be used and are within the scope of this invention. Example 2 below describes an exemplary protocol for the production and purification of avian antibodies against bacterial immunogens. This is merely illustrative and is not meant to be limiting. Deviations from the illustrative example for production and purification are within the scope of this invention.

The antibodies from these preparations may be stored in a liquid form. Preferably the liquid is stored between about 4-8° C. At this temperature, the preparations may be stored for up to about 6 months. Alternatively, the liquid can be further processed by drying or other methods to form a powder. A variety of methods can be used to form a powder and all of these methods are within the scope of this invention. Preferably, the process of forming the powder results in preserving at least about 50 percent of the activity of the antibody, more preferably, at least 70 percent and even more preferably, at least about 90 percent of the activity of the antibody is preserved. Powdered forms can be stable at room temperature for at least 3 years. In some embodiments, the powdered form can be prepared for use by rehydration in acidified water or an acidified buffer. In some embodiments, this rehydrated composition may also be subject to additional purification steps such as the purification steps described above to yield a highly purified antibody preparation.

The anti-toxin composition described herein includes the egg contents or antibody preparations described above. The anti-toxin composition can have antibodies against only one bacterial immunogen, i.e. a monovalent composition. Alternatively, the anti-toxin composition can include antibody preparations that were raised against different bacterial immunogens, but combined into one anti-toxin composition, i.e. a polyvalent composition.

The composition may include additives, carriers and the like in order to improve the utility of the composition during or after administration to a host.

The anti-toxin compositions described herein can be used in a variety of ways. The anti-toxin can be used to bind the bacterial toxins in a host. The anti-toxin composition can be administered to the host orally, nasally or through other routes. Preferably, the administration is oral or nasal. The anti-toxin composition acts in the gut of an animal and reduces the bacterial toxin activity in the gut of an animal. Bacterial toxins in a host can also leak from the GI tract and enter the bloodstream. In such instances, the bacterial toxins can also be neutralized in the bloodstream by the anti-toxin composition surprisingly acting in a systemic manner. This can be particularly effective in reducing a systemic inflammatory response engendered by free bacterial toxins.

In one exemplary embodiment, administration of the anti-toxin composition can lead to a decrease in the inflammatory immune response in an animal. The occurrence of an inflammatory response has been associated with elevated levels of bacterial toxins and thus, administration of the anti-toxin composition can lead to a reduction in the inflammatory response.

Administration of the anti-toxin composition can also decrease the concentration of molecules associated with the inflammatory response. Molecules associated with an inflammatory response include, for example, TNF-$\alpha$c, LBP, CD14, IL1-$\beta$ and the like. In some embodiments, administration of the anti-toxin composition can lead to reduced levels of TNF-$\alpha$. Without being bound by any theory, it is believed that administration of the anti-toxin composition binds the bacterial toxin and reduces the severity of the inflammatory response engendered by the host. The dampened inflammatory response is represented by the lower concentration of the TNF-$\alpha$ found in the bloodstream.

In some embodiments, the anti-toxin composition may be administered to an animal orally. Oral administration may result in directing the antibodies to the GI tract. In the GI tract, the antibodies can agglutinate the toxins and prevent the leakage of the toxin into the bloodstream. Administration of the anti-toxin composition using other routes of delivery are also within the scope of this invention.

Anti-toxin compositions having two or more antibodies may be used against a toxin challenge by one organism. In one exemplary embodiment, a host challenged by Shiga toxin producing *E. coli* (STEC), may be administered an anti-toxin composition that includes antibodies against both endotoxin and Shiga toxin. Anti-toxin compositions containing antibodies against either endotoxin or Shiga toxin alone may be used. Anti-toxin compositions having antibodies against both endotoxin and Shiga toxin can be more protective than administration of the antibodies alone and in fact, can have a synergistic effect. In other words, the use of both antibodies can be more protective than the combined effect of either antibody alone.

In some preferred embodiments, the endotoxin antibodies and Shiga toxin antibodies are raised in different birds and blended together prior to administration into a host challenged by organisms such as STEC. In other preferred embodiments, the endotoxin and Shiga toxin are combined and then used to inoculate birds prior to harvesting eggs for the antibodies. Thus, the birds are immunized with both endotoxin and Shiga toxin together. All of these embodiments can be particularly potent as anti-toxin composition. Other combinations of antibodies against challenges to bacterial toxins or pathogenic bacteria are within the scope of this invention.

In some embodiments, the antibodies in the anti-toxin composition are only to the toxin that is present as a challenge toxin. This is referred to herein as a homologous antibody composition.

The anti-toxin compositions described herein can be used therapeutically against a number of diseases. The anti-toxin composition may also be used prophylactically to prevent or reduce the occurrence of some diseases or metabolic conditions. Administration of the anti-toxin composition can prevent or reduce the occurrence of a number of diseases associated with metabolic syndrome. These diseases include artherosclorosis, diabetus mellitus, insulin resistance, and obesity. Without being bound by any theory, it is believed that occurrence of a number of these diseases is related to a chronic inflammatory type response present in the GI tract and that this chronic inflammatory response is due to the presence of elevated levels of bacterial toxins which may lead to chronic systemic inflammation. Administration of the anti-toxins can reduce the levels of the bacterial toxins and thus, reduce the inflammatory response that occurs in an individual. Similarly other diseases such as fatty liver disease and Crohn's disease may also be associated with elevated levels of toxins engendering an inflammatory response. Thus, individuals having these diseases can also benefit from anti-toxin composition therapy.

The anti-toxin composition may also be used therapeutically, for example, against infections of pathogenic bacteria. Infections by pathogenic bacteria such as *E. coli* 0157, *Klebsiella, H. pylori, C. difficile, S. aureus*, can be serious and sometimes lead to lethal consequences. Treatment of these bacteria can be difficult and the treatment itself can adversely affect the patient. The anti-toxin composition of the present invention can be administered to patients with infections of these bacteria. The use of these anti-toxin compositions can be well tolerated with minimal deleterious effects.

The anti-toxin composition can be administered at regular intervals, for example, daily, weekly, or monthly. Administration of the compositions at regular intervals may be particularly amenable to chronic conditions. The compositions may be also administered multiple times a day, especially in the case of infections by pathogenic bacteria.

Nasal application of the compositions may be more preferable for infections or conditions occurring in the respiratory tract. However, nasal application may also be used for infections in the GI tract or other locations.

EXAMPLES

Example 1

Production of Immunogens

Gram Negative Microorganisms:

Bacteria were grown in MINCA or other suitable media for production of whole cell growth and capsular components. Growth was in either microaerophilic or anaerobic conditions and at temperatures, which were similar to that found in the normal growth site of the organism, i.e. nasal, 34° C. or GI-36-39° C. Standard laboratory methods such as growth at 37° C. were not always suitable. Bacteria were grown on agar plates (150 MM or larger) for production of capsular components and toxin(s). Bacteria were grown in broth (200 ml or larger) in aerobic and/or anaerobic conditions to simulate GI conditions.

Plate cultures were harvested into sterile PBS with a pH at isoelectric point of desired toxin e.g. LPS, isoelectric point (pI) at pH5.01. Similar isoelectric point values were available and were critical to the harvest and recovery of the specific toxin or cellular constituent desired. Whole cells were harvested from both agar plate and broth cultures. Agar Plate cultures were scraped from the agar surface after a quantity of sterile, low pH PBS was used to wash the plate. Broth cultures were decanted into sterile centrifuge tubes and centrifuged at 2500-6000×g to pellet the cells from the liquid medium.

Supernate was decanted into sterile containers for further processing. Whole cell pellets were resuspended into sterile PBS, sampled for cell count and inactivated with formaldehyde or other suitable inactivating agent. This material was transferred to another sterile container and allowed to stir for a minimum of 8 hours or until inactivation was confirmed by lack of growth on Petrifilm™ plates from 3M, St. Paul, Minn. The supernate fluids were further processed by filtration (0.22μ sterile filter) to remove any potential cells.

Fluids were then processed by isoelectric point filtration, for example Pall Mustang Filters with elution at the desired pI of the toxin(s) of the microorganism. Fluids were in some cases also further derived by molecular weight filtration (example, Spin filtration at 50μ, 100μ, or such to separate desired components for further use as immunogens). Both the retentate (larger molecular components) and the effluent (smaller molecular components) were retained for use as specific immunogens. Varied preparations of toxins and/or cellular components were stored in sterile PBS (designated pH) until needed for use but for no more than 6 months at 4-8° C. or frozen at −70° C. for long term storage. They are not to be frozen at −20° C.

Gram positive microorganisms: These cultures were grown in specific media e.g., blood agar, chocolate broth or agar, Todd-Hewitt and high protein agar developed for growth of each microorganism and its production of the desired cellular component or toxin. Agar plate cultures of each organism were prepared as pour or spread plates and cultured in aerobic or anaerobic conditions. Broth cultures of each organism were inoculated as well and cultured in comparable aerobic or anaerobic conditions. Cultures from spore-forming microorganisms were always started from pure spore cultures, not vegetative cells. A spore seed vial was heat shocked at 80°-90° C. for 10-20 minutes to ensure that the viable cells are destroyed.

Spores were stored in solution such as 70-90% Ethyl alcohol to further destroy any vegetative cells. Spores were spun from Ethyl alcohol and washed in sterile PBS 2×. The pellet of spores was added to RCM or correct medium in tube and incubated at appropriate temperature (35°-38° C.) in either aerobic or anaerobic conditions. The spores were cultured for a minimum of 24 hours to ensure vegetative growth. Cell growth was confirmed by spectrophotometry.

After achieving desired cell growth, not exceeding 24 hours or late log phase, the culture was passed into larger volume of medium and cultured under appropriate conditions for up to 5 days, ensuring maximum toxin production. The broth culture was centrifuged in sterile containers at 4500-6000×g for 15-35 minutes. The supernate was removed (sterile filter, 0.22μ), and stored in desired aliquots at 4° C. until needed for use as an immunogen.

Toxin production was confirmed by testing using commercial test ELISA kits, cell cytotoxicity or cell viability assays. Cell cytotoxicity assays that were used include Vero cytotoxicity, L929 cytotoxicity, J774a.1 cytokine activity assay and BL3 Cell Viability. An MTS assay for cell viability was used in conjunction with each of the cytotoxicity tests for further documentation of toxin or peptidoglycan concentration. The MTS reagent kit was obtained from Promega, Madison, Wis., the TNF-α kit was Thermo Scientific, Waltham, Mass. and all cell cultures were obtained from ATCC laboratory. The LAL, chromogenic LAL or other endotoxin (LPS) concentrations were used for each Gram-negative preparation. LPS units for satisfactory harvest must be $1\times10^4$ EU/ml to $3\times10^6$ EU/ml. Assays were performed using kits from Lonza in Allendale, N.J. or Charles River Laboratories, Wilmington, Mass.

The Vero cytotoxicity test was utilized to confirm Shiga toxin production. Satisfactory harvest of STEC had Shiga toxin units at 1000-200,000 units/ml. The Vero or L929 cytotoxicity tests were used to confirm satisfactory production of clostridal toxins. Satisfactory harvests contained 2500-100,000 toxin units/ml. Vero cells test was used in conjunction with MTS cell viability assay to confirm leukotoxin and other toxin suitability. Leukotoxin solutions contained a minimum of 10,000 units/ml to be satisfactory.

Example 2

Production of Avian Antibodies

This Example relates to methods for making antibodies to specific immunogens using whole eggs or egg yolk extracts.

Birds were immunized with a single adjuvanted immunogen over a time course of 4-8 weeks. 10-14 days post-last immunization, eggs were collected for further processing. The egg material was either whole egg (yolk+white) or yolk only. The whole egg or egg yolk were further processed by the addition of acidified water or acidified PBS. This was allowed to stir at 4-8° C. for a minimum of 1-4 hours. Centrifugation, either by fixed angle rotor or continuous flow was performed to remove unnecessary solids. The product was, in some cases, clarified by the use of PEG precipitation, affinity chromatography, or tangential flow filtration (TFF) (specific molecular weight cutoff). Varied eggs were combined to produce the final product. These can be selected from the various groups of eggs containing specific antibodies for a monovalent product or a polyvalent product(s).

All products were produced using a specific amount of egg material suspended and mixed with a low pH (4.5-6.5) PBS to ensure the soluble protein/antibody was thoroughly resuspended in the fluids. The materials were mixed for a minimum of 1 hr to 4 hours to adequately solubilize all proteins/antibodies. All products were pasteurized at a temperature not to exceed 156° F. for 15-30". Material was immediately cooled to 4-8° C. for storage.

Liquid product was stored at 4-8° C. for up to 6 months or further processed to form a powder. The powder was formed by using a spray dry procedure with evaporative drying to maximize retention of antibody activity. This powder was then stable at room temperature for up to 3 years with no loss of antibody activity.

Further product definition and purification was also performed by rehydration of the spray-dried powder with acidified water extraction. This was followed by either or both of continuous flow centrifugation and TFF.

A final purification process of either affinity chromatography and/or tangential flow filtration was used to provide a very pure concentrated antibody product for final lyophilization. The final end product was a lyophilized product delivered for either water delivery (after resuspension) or oral delivery via rapid dissolution in a carrier matrix.

All products were designed to be delivered orally or nasally to provide interaction with the tissues and organs of the Mucosal Associated Lymphoid Tissue and Gut Associated Lymphoid Tissue of the mammalian immune system.

Example 3

Mice and Cytotoxicity Study Models for Toxins

Purpose:

This examples describes procedures to evaluate the toxin components derived from a Shiga toxin producing *E. coli* (STEC) or gram negative bacterium such as *Escherichia coli* o157:H7, in a mouse toxicity model and in a cytotoxicity study.

The potential $LD_{50}$ (dose of toxin inducing 50% lethality) was determined of either a 1:110 or a 1:120 toxin preparation. The toxin extracts and their corresponding whole cell preparations from an *E. coli* o157:H7 were prepared that were used for hyperimmunization of hens. The toxin(s) genes carried by this particular isolate have been determined and verified by varied test methodologies including ELISA, PCR and cell cytotoxicity testing. The isolate was certified as an STEC or Shiga toxin producing *E. coli*. It carried the STx2b toxin gene, an STb1 gene, a leukotoxin gene and an endotoxin gene. Any STEC producing microorganism to be used carried the STx1, STx2 or both of these genes. Additional toxin genes were also necessary for the production of the correct immunogens for production of the avian antibody. All listed isolates below were suitable for this type of work.

a. *Escherichia coli* o157:H7 (013011JH, $4.73\times10^5$ EU/ml)

b. *Escherichia coli* 0141:H (F-18 swine isolate)

c. *Escherichia coli* 0111:B4 ($3.6\times10^6$ EU/ml)

The toxin preparations from each bacterium were used in both the mouse and the cell culture toxicity assays. Varied dilutions were required for each assay. These are noted below. The specific antibody produced against each of the toxin extracts as well as the whole cell preparations were used in the cell culture assays as well. This indicated neutralization of the toxin and helped determine a suitable dose of antibody for mouse studies.

Mouse studies: All work was done with the prime and challenge dose delivered intraperitoneally (IP). All mice were on feed and water for 18-24 hours before trial started. 2 mice were subject to necropsy upon arrival in order to culture for microbial flora and photograph the normal intestinal tract of the naïve mouse. The following day, Day −1, mice were primed. Priming was done by using a 1:10 dilution of the dose used for challenge on day 0. On Day 0, each of mice was challenged with the desired toxin dilution. Necropsy was performed on 5 mice, 1 control and 1 from each 1:10 prime pool. The mice were observed daily for moribund, lethargic or dead mice. Weights of the mice were recorded upon arrival, before challenge, and at end of trial. Necropsy was performed on at least 1 moribund mouse from each extract and the intestinal tract(s) was evaluated.

Daily water and feed intake was recorded. All Dead or moribund mice were recorded each day.

VEROCYTOTOXICITY TEST: Each endotoxin extract was evaluated in the cytotoxicity assay in microtiter plates. Each extract was tested. The toxin solutions were used undiluted and then carried through nine (9) 10-fold dilutions to a final dilution of 1:1080. This was used to determine the endotoxin or toxin lethal dose in a cell culture system. This was a 3-day test. For example, cells were planted on Tuesday and the extracts started on test on Wednesday. Cultures were examined on Thursday and Friday with the latter being termination of the test.

Example 4

Bacterial Toxin Studies in Mice

Swiss Webster white mice, female, at 18-20 grams were used. The mice were housed as sets of 5 mice in each cage, with ad lib feed and water at arrival. They were acclimated for a minimum of 3 days prior to inception of the toxin trial.

Antibody Solution (Anti-Toxin Composition)—

The trial used a prepared solution of extracted avian yolk antibodies, termed Solution 4. This solution 4 contained avian antibodies produced against the following immunogens:

*Escherichia coli* o157:H7 cell wall extracts.

*Escherichia coli* toxin extracts (includes endotoxin and Shiga toxin components)

*Klebsiella pneumoniae* whole cell and endotoxin

*Pseudomonas aeruginosa* whole cell and endotoxin

Solution 4 contained about 50% to 60% by volume of antibody solution and about 40% to 50% by volume of buffer, pH 5.5-6.5. The antibody solution contained equal percentage by protein of the antibodies against each of the immunogen, i.e. 25% of the protein/antibody raised against each of the immunogen.

The solution contained a minimum of 3 mg/ml of antibodies in order to be used for experimental studies. This solution was stored at −20° C. for no more than 6 months or at 4-8° C. for no more than 3 months. The solution was prepared from several types of stock solutions including egg yolk material purified by either PEG extraction or acid water extraction, spray dried whole egg powder extracted with acidified water per the method of Akita, Journal of Food Science, vol. 57, No. 3, 1992.

The antibody solution used for this study was a liquid preparation of the Solution 4 egg yolks. Solution 4 is a combination of purified antibodies from the egg yolks obtained from using the 4 immunogens. The concentration of antibodies in Solution 4 was 3.22 mg/ml. The antibody solution was diluted in sterile PBS to achieve antibody concentrations of 2 mg/ml, 1.5 mg/ml, 1.0 mg/ml, and 0.5 mg/ml.

Toxin for Challenge in Mice—

The toxin preparation was prepared from the material used to hyperimmunize the hens to develop antibodies against *Escherichia coli* o157:H7, cell wall and toxin units. The material was stored at 4-8° C. for a period not to exceed 6 months. The source was either commercial toxin preparations or preparations from isolates grown according the protocols described above in Examples 1. The toxin amount was determined by either chromogenic LAL (endotoxin) or Vero cytotoxicity (Shiga toxin). LAL is the limulous amebocyte lysate test and tests may be obtained, for example, from Lonza, Allendale, N.J. or Charles River Laboratories, Wilmington, Mass.

Specific sets of mice were started on water containing antibodies, 3 days prior to the challenge day. This water was changed daily to provide a consistent, clean preparation to the mice. Feed continued to be ad lib.

Day 0 of trial was day of Intraperitoneal (IP) challenge with the toxin, 0.5 ml delivered to each of the specified mice. Antibody water was continued throughout the 96-hour trial. Morbidity and mortality was measured and recorded each day. The trial was terminated at 96 hours.

The data shown below in Table 5 was from an *Escherichia coli* o157:H7 challenge preparation made according to the procedure in Example 1. The LAL or endotoxin results indicated a 4.73x$10^5$ EU/ml. Studies with dilutions at 1:50, 1:70, and 1:90 showed that these dilutions were too concentrated to determine an $LD_{50}$. In the test results shown below, a greater dilution scheme was used to further determine and evaluate an $LD_{50}$.

These results are shown in Table 5 below. The 1:110 (4.3×$10^3$ EU/ml) toxin dilution exhibited very good protection with the higher dilutions of antibody while the 1:130 (3.6×$10^3$ EU/ml) of toxin itself caused less than 50% death in the mouse. Thus, the dilutions of antibody were very successful in protecting against such a challenge.

TABLE 5

| Toxin dilution | Antibody conc | Dead | Live |
|---|---|---|---|
| 110 TX | 0 Ab | 80% | 20% |
| 110TX | 2.0 Ab | 20% | 80% |
| 110TX | 1.5 Ab | 50% | 50% |
| 110TX | 1.0 Ab | 30% | 70% |
| 110TX | 0.5 Ab | 70% | 30% |
| 130TX | 0 Ab | 40% | 60% |
| 130TX | 2.0 Ab | 0% | 100% |
| 130TX | 1.5 Ab | 10% | 90% |
| 130TX | 1.0 Ab | 30% | 70% |
| 130TX | 0.5 Ab | 30% | 70% |

Example 5

Studies in Mice Using a Homologous Antibody Solution

Swiss Webster white mice, female, at 18-20 grams were used. The mice were housed as sets of 5 mice in each cage, with ad lib feed and water at arrival. They were acclimated for a minimum of 3 days prior to inception of the toxin trial.

This study was a continuation of the *Escherichia coli* o157:H7 studies described above in Example 4. The study was to evaluate lower dilution/greater concentrations of the Shiga toxin-endotoxin preparation made according to the procedures described in Example 1. A prepared solution of extracted homologous avian yolk antibodies was used. This solution contained avian antibodies produced against the following immunogens:

*Escherichia coli* o157:H7 cell wall extracts.

*Escherichia coli* toxin extracts (includes endotoxin and Shiga toxin components)

The antibody solution used for this study included equal percentages of each of the antibodies and was a liquid preparation of the homologous egg yolks. The concentration of antibodies was 3.11 mg/ml. The antibody solution was not diluted in sterile PBS but was used as a 100% antibody solution.

The solution contained a minimum of 3 mg/ml of antibodies in order to be used for experimental studies. This solution should be stored at −20° C. for no more than 6 months or at 4-8° C. for no more than 3 months. The solution may be prepared from several types of stock solutions including egg yolk material purified by either PEG extraction or Acid water extraction, spray dried whole egg powder extracted with acidified water per the method of Akita (see above).

The toxin preparation was prepared from the material used to hyperimmunize the hens to develop antibodies against *Escherichia coli* o157:H7, cell wall and toxin units. The material was stored at 4-8° C. for a period not to exceed 6 months. The source was either commercial toxin preparations or preparations from isolates according to Example 1. The toxin amount was determined by either chromogenic LAL (endotoxin) or Vero cytotoxicity (Shiga toxin).

Specific sets of mice were started on water containing antibodies, 3 days prior to the challenge day. This water was changed daily to provide a consistent, clean preparation to the mice. Feed continues to be ad lib. Day 0 of trial was day of Intraperitoneal challenge, 0.5 ml delivered to each of the specified mice.

Antibody water was continued throughout the 96-hour trial. Morbidity and mortality was measured and recorded each day. The trial was terminated at 96 hours.

The particular *Escherichia coli* o157:H7 challenge preparation was from an isolate according to Example 1. The LAL or endotoxin results were 4.73x$10^5$ EU/ml. The preparation was diluted in commercial endotoxin free water to final use dilution of 1:75 (6.3x$10^3$ EU/ml) and 1:100 (4.73x$10^3$ EU/ml). A challenge dose of 0.5 ml was delivered intraperitoneally to each specific mouse.

The results are shown in Table 6 below. The 1:75 dilution of toxin resulted in 80% death in the non-treated group while the same dilution used in conjunction with the antibody solution, delivered orally, had 50% less death.

The 1:100 dilution of toxin exhibited less death (60%) in the non-treated group in association with greater protection in the oral antibody solution group.

There appears to be a definite dose response with both toxin and antibody within the study.

TABLE 6

| Study 0157:H7 Toxin challenge* | | | |
|---|---|---|---|
| Endo/Shiga toxin | Antibody | Dead | Live |
| 1:75 Tx dilution | 0Ab | 80% | 20% |
| 1:75 Tx Dilution | 100% | 40% | 60% |
| 1:100 tx dilution | 0 ab | 60% | 40% |
| 1:100 Tx dilution | 100% | 20% | 80% |

*Homologous avian antibody concentrate continuously in water for 72 hours prior to challenge

Example 6

*Clostridium difficile* Toxicity and Antibody Neutralization Assays

This example illustrates studies to observe and identify *Clostridium difficile* (C. diff) A and B toxicity and antibody neutralization in 2 cell lines; Vero and L929 fibroblasts.

Materials: Cell Lines—Vero (P159) and L929 (P14) were obtained from ATCC laboratory. Toxin-C. diff ISU #2 072210JF (A and B confirmatory toxin test) were prepared according to example 1. Media-DMEM 2%/1% Calf Serum (CS) with Ampicillin and Gentamicin, DMEM with Ampicillin and Gentamicin, RPMI 1640 5%/1% Fetal Bovine Serum (FBS) with Ampicillin and Gentamicin, RPMI 1640 with Ampicillin and Gentamicin. Antibody: Anti-C. diff IgY, PEG-purified preparation 080310JF, suspended in DMEM prepared according to Example 2 above.

Procedure: Both microtiter plates for the Vero and L929 lines were seeded using 200 uL of [$10^5$ cells/mL]. The seeding media was DMEM with 2% CS (Vero) and RPMI with 5% FBS (L929). In addition to adding 200 uL of cells, specific wells received 50 uL Anti-C. Diff IgY (IgY). After 40 hours at 37° C. 4% $CO_2$, a cellular monolayer had formed for both cell types. The toxin was diluted, using the corresponding media with 1% calf-serum (CS) or fetal bovine serum (FBS), two-fold out to [1:64]. All wells had their maintenance media aspirated and certain wells were given various volumes of IgY. After the addition of IgY, each well received 100 uL of diluted toxin. 100 uL DMEM or RPMI media was also added to the cell control wells. Plates were then incubated at 37° C. 4% $CO_2$.

Figure 1B:
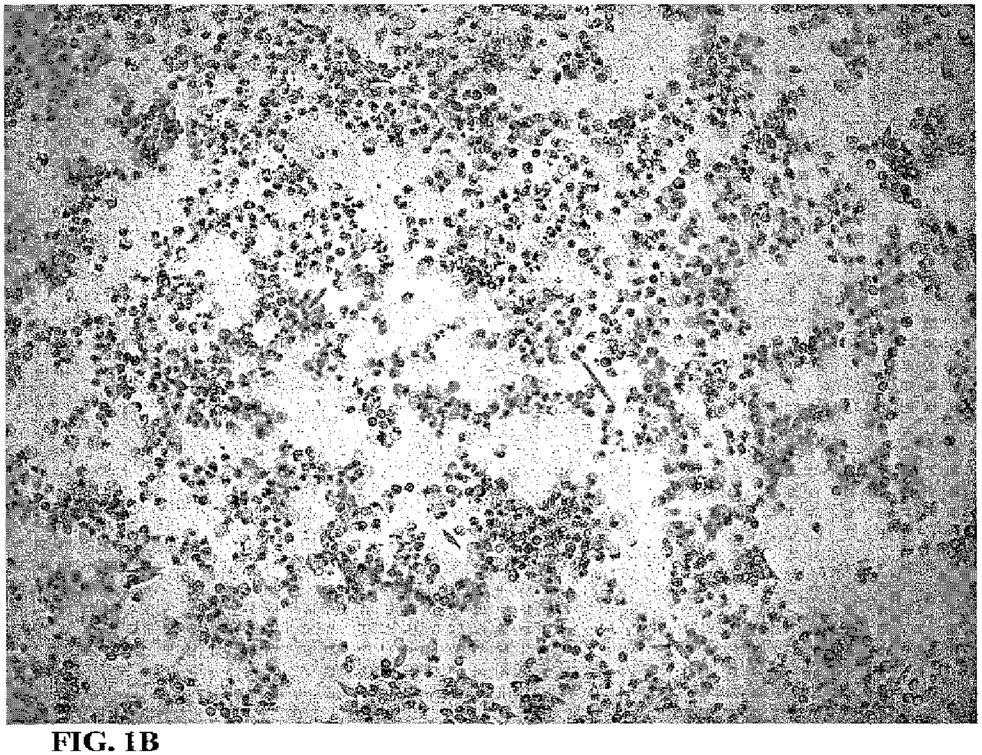
FIG. 1B is a micrograph that shows L929 cells with toxin.
Figure 1C:
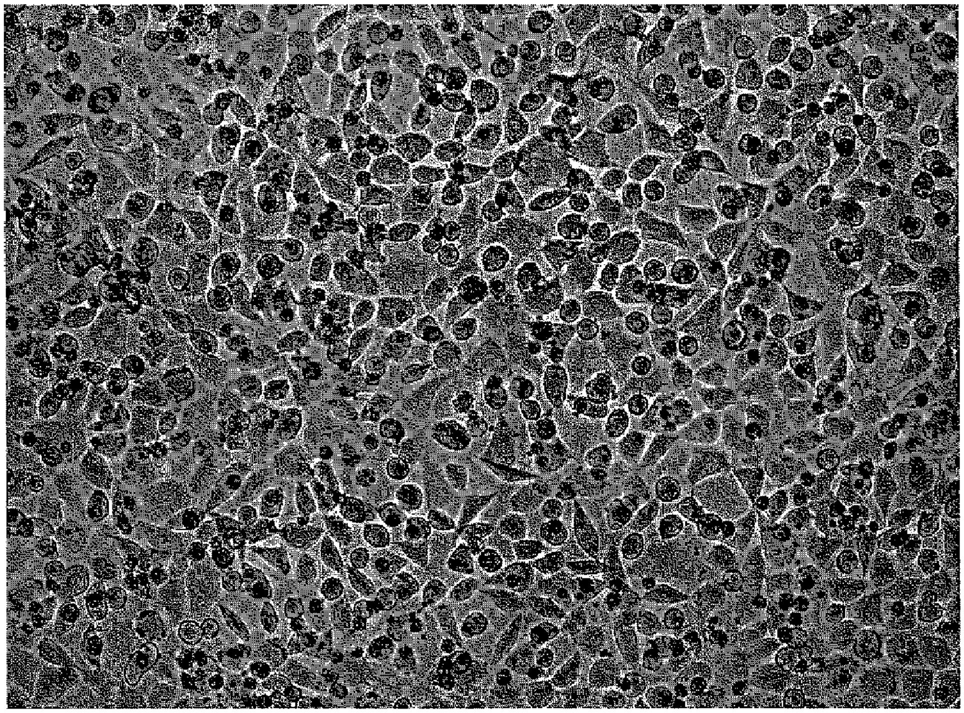
FIG. 1C is a micrograph that shows L929 cells with toxin and antibody.

FIG. 1A is a micrograph that shows an even monolayer of the L929 cells with close cell membrane adhesion and no damage. FIG. 1B is a micrograph that shows extensive damage and death of cells due to the effect of the *C. difficile* toxin solution present in the cell culture well for 24 hrs. There are few viable cells. FIG. 1C is a micrograph that shows a heavy confluent monolayer with little dead cells. In fact, there is an abundance of cells from the effect of the protein from the antibody solution on the cells. The antibody solution has negated the effect of the toxin on the cell culture.

Figure 2:
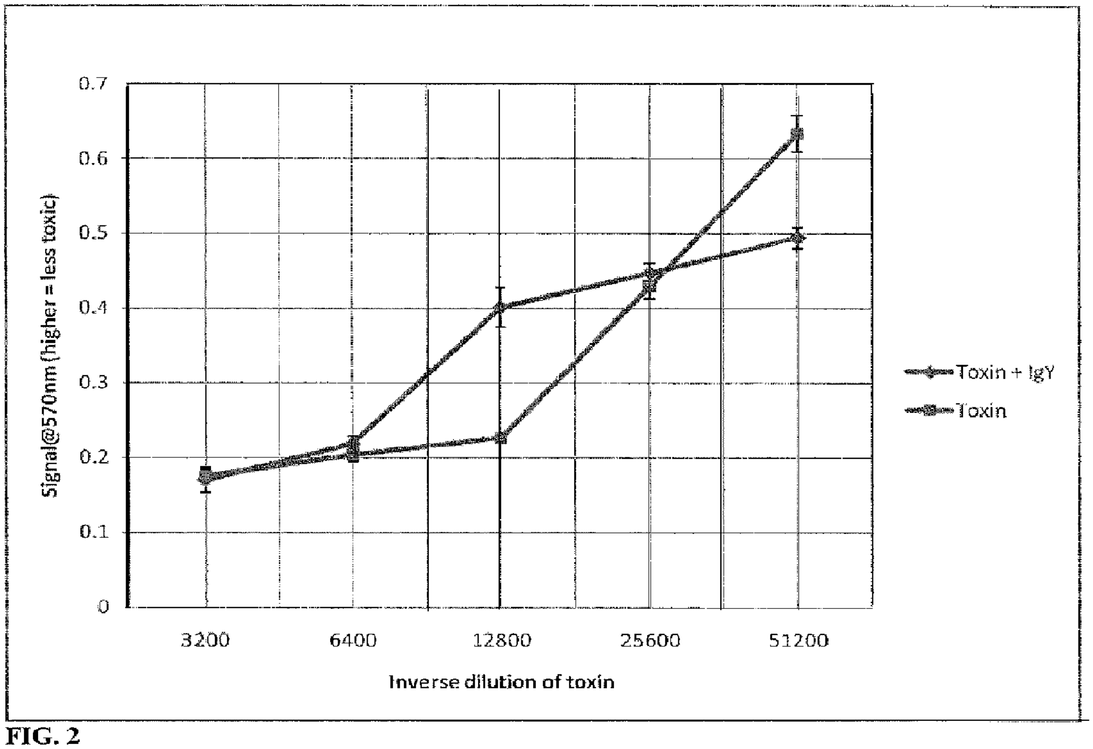
FIG. 2 is a plot of *C. difficile* toxin MTT cell viability assay.

FIG. 2 is a plot of *C. difficile* toxin MTT cell viability assay. The graph depicts a 1 dilution reduction of toxicity from α-*C. difficile* toxin IgY neutralizing both *C. difficile* A and B toxins.

Example 7

Mouse Studies Using *C. Difficile*

Figure 3:
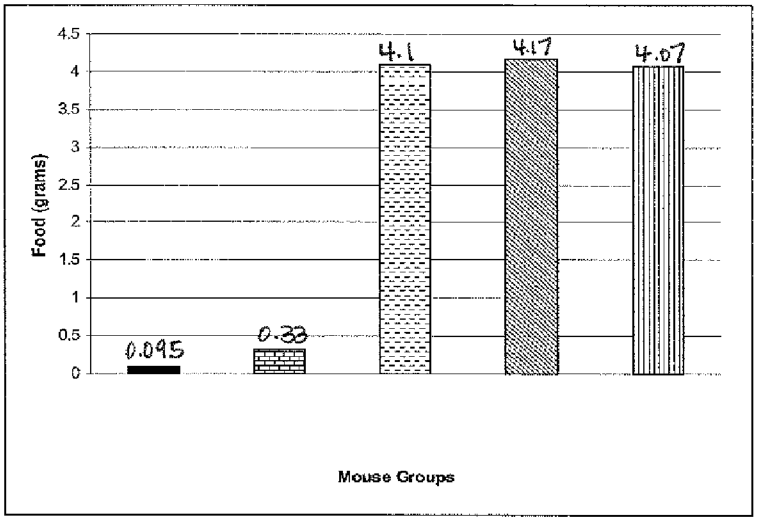
FIG. 3 is a bar graph of feed consumption of mice over 17 hours after administration of different levels of toxin.
Figure 4:
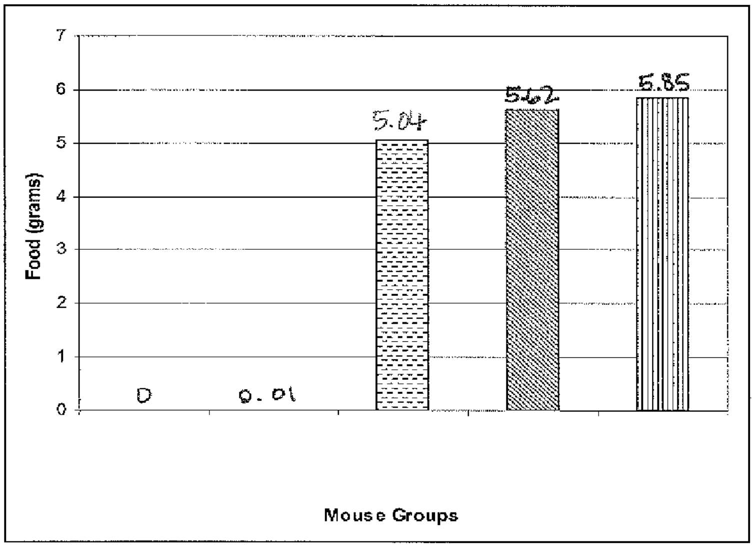
FIG. 4 is a bar graph of feed consumption of mice from 17-41 hours after administration of different levels of toxin.

Mouse studies were performed as described above. Mice were challenged with a *C. difficile* toxin. *C. difficile* unfiltered toxin at its stock concentration was lethal to mice in under 17 hours. See FIG. 3. The toxin diluted 1:10 was lethal between 17-41 hours. Toxin concentrations above 1:10 (1:100 and 1:1,000) were not lethal, and had no impact on feed intake (morbidity marker) after 41 hours. See FIG. 4.

Study 1: *C. difficile* mouse challenge outline: The *C. difficile* toxin was diluted 1:5 in endotoxin-free water (EFW). The diluted toxin was mixed at equal parts with antibody, spray dried whole egg (Start Right*) diluted, also in EFW, 1:10 for an hour at 25° C. The final concentration of toxin is 1:10, and antibody concentration was 1:20. 500 uL was injected IP. The study time frame was 48 hours post injection, and then extended out to 144 hours. *Spray dried whole egg powder produced from hen egg where hens were immunized with either *Clostridium difficile, Clostridium perfringens* A or toxin preparations of each of these microorganisms. Toxin portion of each preparation was confirmed by either ELISA or cytotoxicity testing in VERO cell culture or other defined method. Table 7 shows the test groups.

TABLE 7

| Cage ID | Group | # of mice | Details |
|---|---|---|---|
| 1 | SP13 + toxin | 5 | Mixed @ 25 C. for 1 hour |
| 2 | H2O + toxin | 5 | Mixed @ 25 C. for 1 hour |
| 3 | SP13 + H2O | 1 | Mixed @ 25 C. for 1 hour |
| 4 | H2O | 1 | Mixed @ 25 C. for 1 hour |

Table 8 shows the results.

TABLE 8

| Time post injection | Mouse weight by cage | Food weight | # alive | # dead |
|---|---|---|---|---|
| CAGE 1 | | | | |
| T0 | 131 g | N/A | 5 | 0 |
| T20.5 | 128 g | 129 g | 5 | 0 |
| T24.25 | 126 g | 129 g | 5 | 0 |
| T44.25 | 107 g | 124 g | 4 | 1 |
| T49.5 | 106 g | 124 g | 4 | 1 |
| T69.3 | 79 g | 120 g | 3 | 2 |
| T73.5 | 51 g | 120 g | 2 | 3 |
| T120 | 27 g | 106 g | 1 | 4 |
| T144 | 28 g | N/A | 1 | 4 |
| CAGE 2 | | | | |
| T0 | 127 g | N/A | 5 | 0 |
| T20.5 | 122 g | 152 g | 5 | 0 |
| T24.25 | 121 g | 151 g | 5 | 0 |
| T44.25 | N/A | N/A | 0 | 5 |
| T49.5 | N/A | N/A | 0 | 5 |
| T69.3 | N/A | N/A | 0 | 5 |
| T73.5 | N/A | N/A | 0 | 5 |
| T120 | N/A | N/A | 0 | 5 |
| T144 | N/A | N/A | 0 | 5 |
| CAGE 3 | | | | |
| T0 | 23 g | N/A | 1 | 0 |
| T20.5 | 23 g | 50 g | 1 | 0 |
| T24.25 | 22 g | 50 g | 1 | 0 |
| T44.25 | 23 g | 46 g | 1 | 0 |
| T49.5 | 23 g | 45 g | 1 | 0 |
| T69.3 | 24 g | 41 g | 1 | 0 |
| T73.5 | 23 g | 41 g | 1 | 0 |
| T120 | 24 g | 30 g | 1 | 0 |
| T144 | N/A | N/A | 1 | 0 |
| CAGE 4 | | | | |
| T0 | 28 g | N/A | 1 | 0 |
| T20.5 | 29 g | 41 g | 1 | 0 |
| T24.25 | 28 g | 41 g | 1 | 0 |
| T44.25 | 28 g | 37 g | 1 | 0 |
| T49.5 | 27 g | 37 g | 1 | 0 |
| T69.3 | 28 g | 32 g | 1 | 0 |
| T73.5 | 27 g | 32 g | 1 | 0 |
| T120 | 28 g | 21 g | 1 | 0 |
| T144 | N/A | N/A | 1 | 0 |

Figure 5:
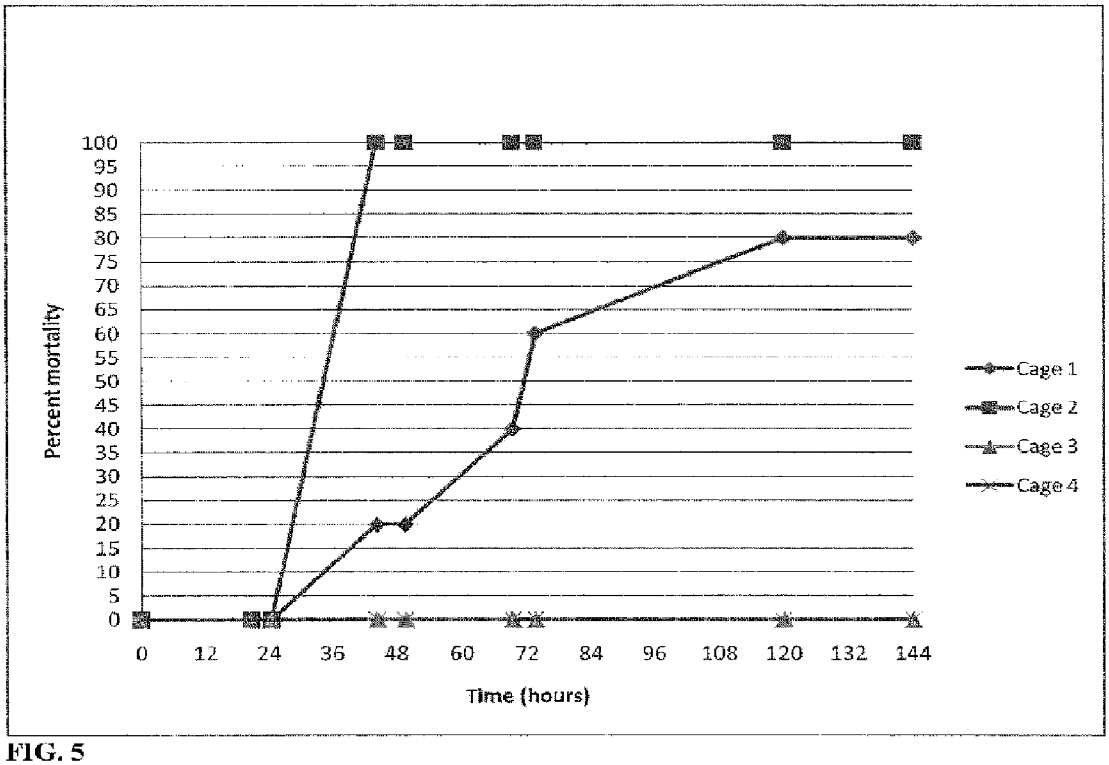
FIG. 5 is a plot of mortality of mice over time after administration of toxin or toxin with antibody.

FIG. 5 illustrates the results from Table 8. *C. difficile* toxin at a diluted concentration of 1:10 had been 100% lethal between time points 24 and 44 hours post injection. The same concentration of toxin, when given with spray dried whole egg powder containing avian antibodies, had a reduced and prolonged timeline mortality rate.

Example 8

Use of LPS to Stimulate Cytokines in Mouse Macrophage (J774a.1) Cell Line

The J774A.1 cell line was known to produce several cytokines, such as TNF-α and IL-1β, when stimulated with bacterial lipopolysaccharide (LPS). This study was done to determine if the toxin preps derived from isolates of *Klebsiella pneumonia* (lot 062711 MH) stimulate the production of these cytokines. Induction of cytokines was examined over a time course of 30 minutes to 8 hours. Commercial Elisa tests for TNF-α were used to test all samples for the presence of each.

Study 1:

Procedure: *Klebsiella pneumoniae* endotoxin solution at a dilution of 1:50 (DMEM without serum or antibiotics) was used in conjunction with the homologous antibody solution. The test cells were J774A.1 seeded on 96-well microtiter plates in DMEM medium+5% FBS and antibiotics. The cells on plates were incubated at 37° C. for 24 hours.

A single dilution (1:100) of the toxin prep was made in DMEM medium without any additives. The dilutions of toxin (1:100 dilution was 1770 EU/ml) and antibody solution was used. The endotoxin results from the LAL test indicated that the *Klebsiella pneumonia* prep contains $1.77\times10^5$ EU/ml.

The dilution of the antibody solution was made in snap cap tubes with sufficient volume or samples to perform all test parameters. All media was removed from each plate. An aliquot (0.2 ml) of each solution/dilution was added to 5 rows×8 wells of the plate. The 6th row was left with only culture medium as a cell control. Therefore, plate 1 contained samples of dilution 1:100 endotoxin in wells 1-5 and 1:100 endotoxin plus dilutions of 1:4 (antibody) in columns 7-9. The endotoxin dilution was added to all wells and allowed to incubate for 30 minutes. After 30 minutes, the first rows (1 and 7) were aspirated and labeled as samples 30-1 tx and 30-1 Ab. All remaining columns were then sampled as noted in the time line. Upon sampling and refeeding of all wells, the medium to refeed the toxin only cells did not contain more endotoxin; however, the antibody-containing wells were refed with medium containing the 1:4 dilution of antibody throughout the timeline of the trial.

All materials in each row (8 wells) represent replicates of a specific dilution or dilution/solution. The supernate from these 8 wells was removed and pooled as one sample. This was done for the dilution/antibody solutions preps and the cell controls noted above. After removal and storage in sterile plastic snap cap tubes, the samples were transferred to a storage box and immediately frozen to stop any further enzymatic activity and until testing is conducted. This step was done post each time sample interval. All sampling was done as described.

Results: The addition of homologous antibody to the wells containing endotoxin does reduce or affect the production of TNF-α by the J774A.1 cells. The homologous antibody was able to bind or neutralize the endotoxin thus potentially reducing the effect of TNF-α.

Study 2:

Determination of dose relationship of toxin to avian antibody. The J774A.1 cell line (murine macrophage) has shown that upon exposure to endotoxin (*Klebsiella pneumoniae*) and to peptidoglycan (*Staphylococcus aureus*), the cells provide both visual and chemical responses.

This study used a commercial preparation of endotoxin from *E. coli* 0111:B4 ($3.0\times10^6$ EU/ml) from Sigma Chemical and *Klebsiella pneumoniae* ($1.5\times10^6$ EU/ml) from Sigma Chemical to determine a dose response curve with homologous avian antibodies. The hens were immunized with preparations of these specific endotoxins. The antibodies were water purified and not PEG purified this time. The concentration of each of these is 5 mg/ml of protein.

This test was conducted with 3 varying toxin preps. The endotoxin was diluted in 3 sequential 1:10 dilutions, going to an estimated $10^{-3}$ dilutions. Each toxin was conducted on separate plates for consistency. Each homologous antibody solution was diluted at 1:2, 1:4, 1:8 for studies with the endotoxin.

The results from the use of the LPS from *Escherichia coli* 0111:B4 (Sigma, USA) in the assay with homologous avian antibody were definite in showing the ability of the avian antibody to bind the toxin and to reduce the effects of such toxin in a macrophage cell line (J774A.1). The greatest dilution of the antibody 1:2 (1.6 mg/ml of protein/antibody) successfully reduced or prevented the production of TNF-α at 3 differing levels of endotoxin. See Table 9. As the dilution of antibody increased, i.e. lesser antibody per ml, the effect was much the same. Therefore, in the presence of homologous avian antibody, it was possible to reduce or prevent the production of the cytokine(s) cascade within the cell culture.

TABLE 9

J774a.1 TNF-α Assay results
4 HRS. POST-CHALLENGE

| | Anti-*E. coli* 0111:B4 antibodies (Pg/ml) | | | |
|---|---|---|---|---|
| Endotoxin* (EU/ml) | 0 | 1:02 | 1:04 | 1:08 |
| 0 | 0 | 0 | 0 | 0 |
| 6,000 | 837.7 | 239.6 | 312.4 | 357.9 |
| 60,000 | 729 | 237.8 | 310.9 | 370.9 |
| 600,000 | 1057 | 277.1 | 359.8 | 416.9 |

**Escherichia coli* 0111:B4 (Sigma)

Example 9

Endotoxin Studies in Mice

Evaluation of Commercial *Klebsiella pneumoniae* Endotoxin Transduction in Mice Via IP Challenge.

Previous trials have shown that there was transit of LPS into the blood system. Standardized, commercial preparation of pure LPS (Sigma) was used to indicate that the LPS does cross the blood barrier and can be found in the portal blood leading from the mesenteric/gut system into the liver. It was known from literature that the LPS can be found in portal blood and can be quantitated from that source.

This study shows that the LPS, administered IP, does transit across the tight junctions of the GI tract and bind to or mix with the avian antibody solution comprising of the materials in Table 10. The preparations of immunogens were performed as described in Example 1.

TABLE 10

| Antigen for immunization | Type of preparation | Percentage of solution |
|---|---|---|
| *Klebsiella pneumoniae* | Whole cell (does contain LPS) | 20% |
| *Klebsiella pneumoniae* | Endotoxin prep | 20% |
| *E. coli* 0157:H7 | Whole cell (does contain LPS/Shiga toxin | 20% |
| *E. coli* 0157:H7 | Toxin (predominantly Shiga) | 20% |
| *Pseudomonas aeruginosa* | Whole cell and LPS | 20% |

The mice were placed into cages upon arrival. Specific cages were set up with Antibody Solution 4 water upon arrival. All other cages were on standard drinking water. Challenge was prepared from *Klebsiella pneumoniae* endotoxin concentrate purchased from Sigma. The endotoxin quantity, per mg, noted by the company was $1.5\times10^6$ EU/mg. Each mouse was given ½ ml of a 1-mg solution, intraperitoneally.

Portal bleeding started 15 minutes post-challenge. A set of mice was sacrificed at specific time points and the blood drawn from the portal vein. Blood from a cage of 5 mice was pooled in order to achieve a large enough quantity for all laboratory work. The blood samples were allowed to sit at RT for 15-30 minutes to coagulate and then were centrifuged in the microfuge. The sera was decanted and stored in micro-centrifuge tubes and flash frozen in liquid nitrogen for transport to the laboratory.

Each sample was tested for LAL, TNF-α, CD14, LBP (lipopolysaccharide protein). The reported cascade was LPS entering the blood stream, binding with LBP, signaling the CD14 for the induction of TNF-α.

Figure 6:
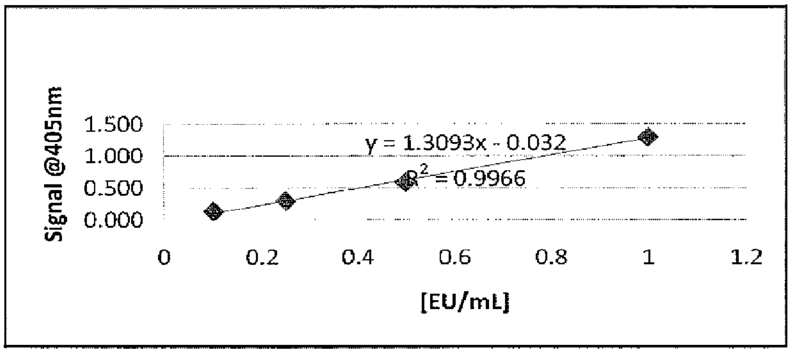
FIG. 6 is a plot of endotoxin reference standard.
Figure 7:
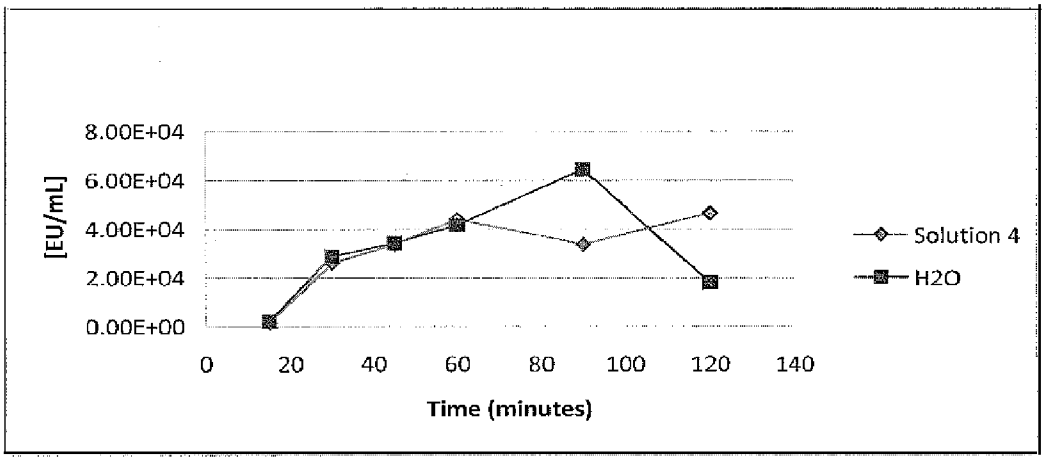
FIG. 7 is a plot of endotoxin concentration over time with or without a protective antibody solution.

The laboratory was able to effectively determine the LPS load in the sera from these mice. FIG. 6 shows a standard curve for determining endotoxin concentration. FIG. 7 shows that the presence of the antibody reduces the endotoxin concentration and is protective over time. The TNF-α test indicates that the higher the EU/ml, the greater the TNF-α that can be detected. Both results do show that the presence of Antibody solution 4 within the lumen of the GI tract does mitigate or reduce the level of TNF-α produced.

Use of the very high concentration of the purified endotoxin was in excess and this was demonstrated by the amount of endotoxin that could or did transit into the blood. This level was extremely high.

A second trial was set up using the same commercial endotoxin preparation. The LPS was at differing dilutions. Antibody water was delivered to a set of mice the day of arrival or a minimum of 3 days before the trial starts. The LPS dilutions were delivered IP, both with and without antibody solution. Mice were bled at same time points, post-challenge. The presence of TNF-α from these sera samples was determined and shown in Table 11.

TABLE 11

| Sample | [TNFα] (pg/ml) |
|---|---|
| Kleb Control | 0 |
| Kleb 15 min. | 0 |
| Kleb 30 min. | 0 |
| Kleb 45 min. | 127.9090909 |
| Kleb 60 min. | 319.2727273 |
| Kleb 90 min. | 2890.636364 |
| Kleb 120 min. | 103.3636364 |
| Kleb 15 min. Sol. 4 | 0 |
| Kleb 30 min. Sol. 4 | 4.727272727 |
| Kleb 45 min. Sol. 4 | 92.90909091 |
| Kleb 60 min. Sol. 4 | 611.5454545 |
| Kleb 90 min. Sol. 4 | 1074.272727 |
| Kleb 120 min. Sol 4 | 377.4545455 |
| Kcal Control | 0 |

Addition of antibody showed some protection against increased levels of TNF-α.

Example 10

Leukotoxin Studies in Cell Culture

*Mannheimia haemolytica*, a member of the Pasteurellaceae family, produces a potent leukotoxin in the nasal pharynx of the mammal. This leukotoxin can be very damaging to the epithelial cells of the same area and allows the bacterium to become carried by the circulatory and other systems into the lungs, causing pulmonary problems.

Figure 8:
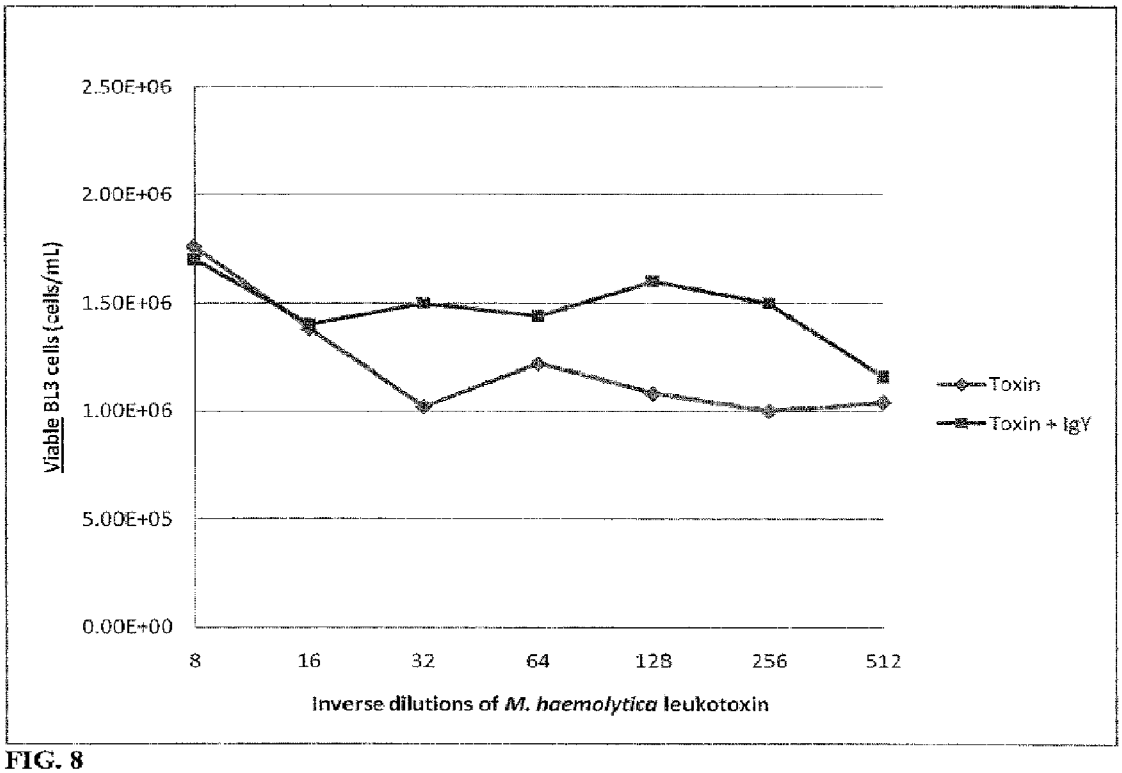
FIG. 8 is a plot of viable BL3 cell count in a *M. haemolytica* leukotoxin assay.
Figure 9:
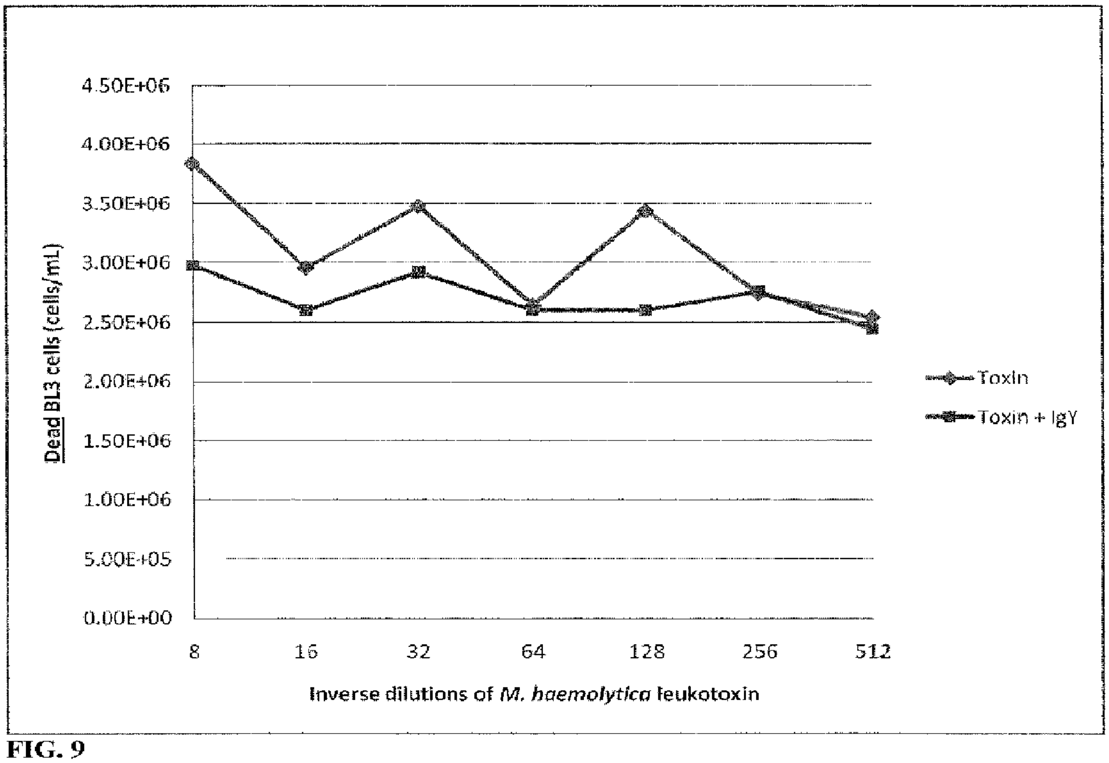
FIG. 9 is a plot of dead BL3 cell count in a *M. haemolytica* leukotoxin assay.

The study described here shows the effect of the avian antibody, produced by the use of *Mannheimia haemolytica* leukotoxin as an immunogen. The BL3 cells are bovine lymphatic cells that grow in suspension culture. In the presence of leukotoxin, the cells do die. This assay indicated that the use of the homologous antibody (anti-toxin) solution did mitigate the effect of the leukotoxin on the BL3 cells. This is reflected by the BL3 viable cell count, as shown in FIG. 8, showing a higher viable cell count in the wells versus just leukotoxin alone. FIG. 9 shows the higher dead cell count of BL3 cells in wells without anti-toxin versus wells treated only with leukotoxin and homologous antibody (anti-toxin).

Although the present invention has been described with reference to preferred embodiments, workers skilled in the art will recognize that changes may be made in form and detail without departing from the spirit and scope of the invention.

What is claimed is:

1. A method of reducing bacterial toxins in an animal comprising administering an anti-toxin composition comprising avian antibodies derived from the egg contents of a bird immunized with an inoculum comprising bacterial toxins harvested and recovered from cells at about the isoelectric point of the bacterial toxins, wherein the antibodies bind the bacterial toxins and wherein the bacterial toxins are endotoxin and Shiga toxin.

2. The method of claim 1 wherein the inoculum comprises purified preparations of the bacterial toxins, cell fragments with the bacterial toxins, whole cells with the bacterial toxins, portions of a bacterial toxin or combinations thereof.

3. The method of claim 1 wherein the bacterial toxins further includes leukotoxin, peptidoglycans, capsular polysaccharides, Toxin A, Toxin B or combinations thereof.

4. The method of claim 1 wherein the inoculum comprises more than one bacterial toxin.

5. The method of claim 1 wherein the antibodies bind more than one bacterial toxin.

6. The method of claim 1 wherein the antibodies bind bacterial toxins on Shiga Toxin producing *Escherichia coli.*

7. The method of claim 1 wherein the antibodies bind the bacterial toxins in the gastrointestinal tract.

8. The method of claim 1 wherein the administration of the composition decreases the inflammatory response in the animal.

9. The method of claim 1 wherein the administration of the composition decreases the concentration of molecules associated with an inflammatory response.

10. A method of reducing bacterial toxins in an animal comprising administering an anti-toxin composition comprising avian antibodies derived from the egg contents of a bird immunized with an inoculum comprising bacterial toxins harvested and recovered from cells at about the isoelectric point of the bacterial toxins, wherein the antibodies bind the bacterial toxins and wherein the administration of the composition decreases the concentration of molecules associated with an inflammatory response wherein the molecules are TNF-α, lipopolysaccharide binding protein (LBP), CD14, IL1-β or combinations thereof.

11. The method of claim 10 wherein the inoculum comprises purified preparations of the bacterial toxins, cell fragments with the bacterial toxins, whole cells with the bacterial toxins, portions of a bacterial toxin or combinations thereof.

12. The method of claim 10 wherein the inoculum comprises more than one bacterial toxin.

13. The method of claim 10 wherein the antibodies bind more than one bacterial toxin.

14. The method of claim 10 wherein the antibodies bind the bacterial toxins in the gastrointestinal tract.

15. The method of claim 10 wherein the administration of the composition decreases the inflammatory response in the animal.

16. The method of claim 10 wherein the administration of the composition decreases the concentration of molecules associated with an inflammatory response.

17. A method of reducing bacterial toxins in an animal comprising
administering an anti-toxin composition comprising avian antibodies derived from the egg contents of a bird immunized with an inoculum comprising bacterial toxins harvested and recovered from cells at about the isoelectric point of the bacterial toxin, wherein the antibodies bind the bacterial toxin wherein the bacterial toxins are from *Escherichia coli, Helicobacter pylori, Klebsiella pneumoniae, Mannheimia haemolytica, Biebersteinia trehalosi, Actinobacillus suis, Haemophilus parasuis, Pasteurella multocida, Fusobacterium necrophorum, Streptococcus pyogenes, Staphylococcus hyicus, Staphylococcus aureus, Streptococcus suis, Streptococcus iniae, Streptococcus agalactiae, Clostridium difficile, Clostridium perfringens, Mycoplasma hyosynoviae, Mycoplasma bovis, Mycoplasma hyopneumoniae* and combinations thereof.

18. The method of claim 17 wherein the inoculum comprises purified preparations of the bacterial toxins, cell fragments with the bacterial toxins, whole cells with the bacterial toxins, portions of a bacterial toxin or combinations thereof.

19. The method of claim 17 wherein the inoculum comprises more than one bacterial toxin.

20. The method of claim 17 wherein the antibodies bind more than one bacterial toxin.

21. The method of claim 17 wherein the antibodies bind the bacterial toxins in the gastrointestinal tract.

22. The method of claim 17 wherein the administration of the composition decreases the inflammatory response in the animal.

23. The method of claim 17 wherein the administration of the composition decreases the concentration of molecules associated with an inflammatory response.

24. A method of treating a disease comprising administering an anti-toxin composition comprising avian antibodies derived from the egg contents of a bird immunized with an inoculum comprising a bacterial toxin harvested and recovered from cells at about the isoelectric point of the bacterial toxin, wherein the disease is caused by increased levels of bacterial toxins wherein the administration of the composition decreases the concentration of molecules associated with an inflammatory response and wherein the molecules are TNF-α LBP, CD14, IL1-β or combinations thereof.

25. The method of claim 24 wherein administration of the composition binds the bacterial toxins in the animal.

26. The method of claim 24 wherein the administration of the composition decreases the inflammatory response in the animal.

27. A method of treating a disease comprising administering an anti-toxin composition comprising avian antibodies derived from the egg contents of a bird immunized with an inoculum comprising a bacterial toxin harvested and recovered from cells at about the isoelectric point of the bacterial toxin, wherein the disease is caused by increased levels of bacterial toxins and is associated with metabolic syndrome.

28. A method of treating a disease comprising administering an anti-toxin composition comprising avian antibodies derived from the egg contents of a bird immunized with an inoculum comprising a bacterial toxin harvested and recovered from cells at about the isoelectric point of the bacterial toxin, wherein the disease is artherosclorosis, insulin resistance, diabetes mellitus, obesity, fatty liver disease, Crohn's disease or combinations thereof.

29. A method of treating a disease comprising administering an anti-toxin composition comprising avian antibodies derived from the egg contents of a bird immunized with an inoculum comprising bacterial toxins harvested and recovered from cells at about the isoelectric point of the bacterial toxin, wherein the disease is caused by increased levels of bacterial toxins and wherein the bacterial toxins are endotoxin and Shiga toxin.

30. The method of claim 29 wherein the antibodies bind the bacterial toxins on STEC.

* * * * *